United States Patent [19]
Zhang et al.

[11] Patent Number: 6,022,977
[45] Date of Patent: *Feb. 8, 2000

[54] DYNAMIC RESOLUTION OF ISOXAZOLINE THIOESTERS TO ISOXAZOLINE CARBOXYLIC ACIDS

[75] Inventors: Lin-Hua Zhang, New Fairfield, Conn.; Luigi Anzalone, West Chester, Pa.; Jaan A. Pesti, Wilmington; Jianguo Yin, Hockessin, both of Del.

[73] Assignee: DuPont Pharmaceuticals Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/047,555

[22] Filed: Mar. 25, 1998

Related U.S. Application Data

[60] Provisional application No. 60/042,109, Mar. 26, 1997.
[51] Int. Cl.$^7$ .................................................. C07D 261/04
[52] U.S. Cl. ........................ 548/240; 548/243; 548/244; 548/245; 548/246
[58] Field of Search ...................................... 548/240, 243, 548/244, 245, 246

[56] References Cited

U.S. PATENT DOCUMENTS

| | | | |
|---|---|---|---|
| 4,256,898 | 3/1981 | Kelly et al. | 548/240 |
| 4,933,464 | 6/1990 | Markifsky | 548/247 |
| 4,952,700 | 8/1990 | Markofsky et al. | 548/240 |
| 4,970,297 | 11/1990 | Castelhano et al. | 530/331 |
| 5,446,056 | 8/1995 | Wityak et al. | 514/340 |
| 5,489,562 | 2/1996 | Burdge et al. | 504/117 |

FOREIGN PATENT DOCUMENTS

| | | |
|---|---|---|
| WO9514680 | 6/1995 | WIPO . |
| WO9514683 | 6/1995 | WIPO . |
| Wo9514681 | 6/1995 | WIPO . |
| WO9524398 | 9/1995 | WIPO . |
| WO9638426 | 12/1996 | WIPO . |

OTHER PUBLICATIONS

Stecher et al. Synthesis, (Jan. 1997) pp. 1–16.
Inagaki et al. J. Org. Chem. (1992) 57, pp. 5643–5649.
Dinh et al. (1996) Tetrahedron Letters, vol. 37, No. 42, pp. 7623–7626.
Fülling et al. (1987) J. Am. Chem. Sci., vol. 109, pp. 2845–2846.
Tan et al. (1995) J. Am. Chem. Soc., 117, pp. 9093–9094.
Zhang et al. (1996) Tetrahedron Letters, vol. 37, No. 26, pp. 4455–4458.
Armstrong et al. (1994) Tetrahedron Letters, vol. 35, No. 20, pp. 3239–3242.
Sih et al. (1989) Topics Stereochemistry, 19, pp. 63–125.
Gombos et al. (1989) J. Chem. Soc. Perkin Trans. I, p. 1915–1921.

*Primary Examiner*—Joseph K. McKane

[57] ABSTRACT

The present invention relates generally to a novel method for preparation of substituted isoxazolin-5-yl acetic acid in high optical purity from a stereoisomeric mixture of an esterified substituted isoxazolin-5-yl acetate. The products are useful in the synthesis of compounds for pharmaceuticals, especially the treatment of thrombolytic disorders, and agricultural products.

25 Claims, No Drawings

DYNAMIC RESOLUTION OF ISOXAZOLINE THIOESTERS TO ISOXAZOLINE CARBOXYLIC ACIDS

This application claims the benefit of U.S. Provisional Application No. 60/042,109, filed Mar. 26, 1997.

FIELD OF THE INVENTION

The present invention relates generally to a novel method for preparation of substituted isoxazolin-5-yl acetic acid in high optical purity from a stereoisomeric mixture of an esterified substituted isoxazolin-5-yl acetate. The products are useful in the synthesis of compounds for pharmaceuticals, especially the treatment of thrombolytic disorders, and agricultural products.

BACKGROUND OF THE INVENTION

Enzymatic resolution of prochiral and racemic compounds has become a valuable and widespread technique, (C. H. Wong, G. M. Whitesides, *Enzymes in Synthetic Organic Chemistry*, 1994, Pergamon Press, New York). There are a variety of methods available for the resolution of racemic or diasteromeric mixtures of molecules which include esterification, de-esterification, acylation, de-acylation, hydrolysis and reduction. Either the desired or undesired isomer may undergo the chemical change as long as the reaction is sufficiently selective for that isomer. Typically, a preparation of a chiral molecule may proceed by the conversion of one of the enantiomers or diasteriomers of a mixture with the correct enyzme. However, simple enzymatic resolutions are restricted to providing a maximum 50% yield of the optically pure product based on racemic starting material. Either the wrong isomer must now be discarded or it is racemized back to a mixture similar to the original mixture. The racemized mixture may now be resubmitted to the enyzmatic resolution conditions as before. Assuming the yield of conversion and recovery to be 100%, the original mixture could be converted to the desired chiral isomer in a time consuming reiterative fashion, each step converting 50% of the racemic starting material of that step. The overall yield would asymptotically approach 100% if the process was infinitely continued. However, in practice, this is rarely possible due to the tedious repeated operations and losses during isolation.

Isoxazolines are important components in pharmaceutically active and agriculturally active compounds. Published examples of active isoxazoline compounds or processes for making isoxazoline compounds include, but are not limited to, U.S. Pat. No. 4,970,297 (transglutaminase inhibitors), U.S. Pat. No. 5,489,562 (herbicides), U.S. Pat. No. 4,256,898 (antitumor and antimicrobials), U.S. Pat. No. 4,933,464, U.S. Pat. No. 4,952,700, PCT International Publication WO 95/14681 (antiinflammatory agents), PCT International Publication WO 95/14680 (antiinflammatory agents), and PCT International Publication WO 95/24398 (inhibitors of TNF release).

Compound (X), is a useful antagonist of the platelet glycoprotein IIb/IIIa fibrinogen receptor complex.

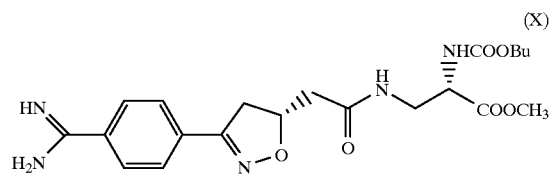

(X)

As such compound (X) is useful in the inhibition of platelet aggregation, as a thrombolytic, and/or the treatment of thrombolytic disorders. The preparation of compound (X) has been disclosed in the following references: U.S. Pat. No. 5,446,056, herein incorporated by reference, PCT International Publication WO 95/14683, PCT International Publication WO 96/38426 and Zhang et al. *Tetrahedron Lett.* 1996, 37, 4455–4458. These documents describe the key role played by compound (R)-(IIa) as an intermediate in the total synthesis of compound (X).

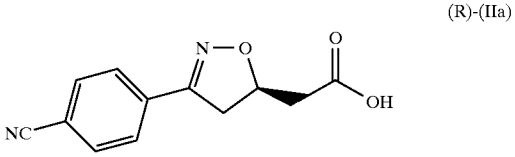

(R)-(IIa)

The current synthetic route to compound (R)-(IIa) consists of an enzymatic resolution of isoxazoline isobutyl oxoesters. The unhydrolyzed ester is then racemized in a second discrete step and resubmitted to hydrolysis conditions. Several repetitions of these two independent reactions eventually yield high conversions of compound (R)-(IIa) but will require an inconveniently large number of isolations and individual reactions (Scheme A).

Scheme A

STEP 1

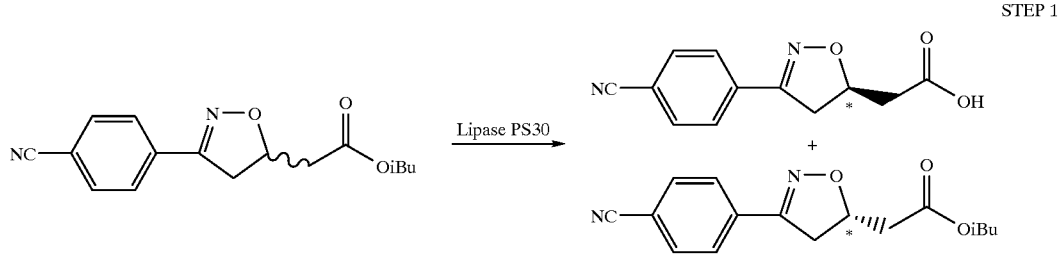

STEP 2

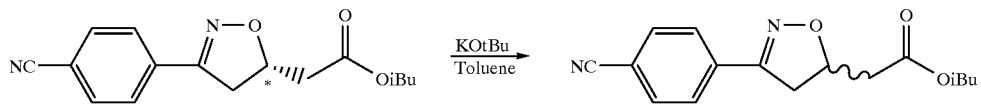

The instant invention achieves the above two step transformations in a single step. Hydrolysis and racemization occur simultaneously by the use of a thioester in place of the oxoester and modification of the reaction conditions, permitting the isolation of compound (R)-(IIa) in one step in equivalent purity and higher yield as compared to the original preparation.

D. G. Drueckhammer, et al., *J. Am. Chem. Soc.* 1995, 117, 9093–9094, have achieved simultaneous hydrolysis and racemization where the chiral center is the alpha carbon to a thioester. In their work, the alpha proton's acidity is enhanced by the presence of an alpha phenylthio group in addition to a thioester. This enables racemization and hydrolysis to occur at similar rates to produce a >99% conversion to the desired product (R)-2, (Scheme B). Drueckhammer, et al. acknowledge that a thioester of a substrate having only saturated alkyl substituents on the alpha carbon would not be sufficiently acidic to permit racemization under the conditions used in their work.

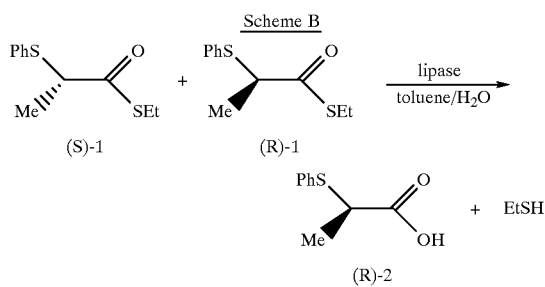

Scheme B

The instant invention concerns the beta carbon whose proton acidity is less then the alpha carbon proton. Therefore, it is hypothesized that racemization at the beta carbon, enhanced by the thioester, proceeds under basic pH by a mechanism of isoxazoline ring opening at the carbon oxygen bond.

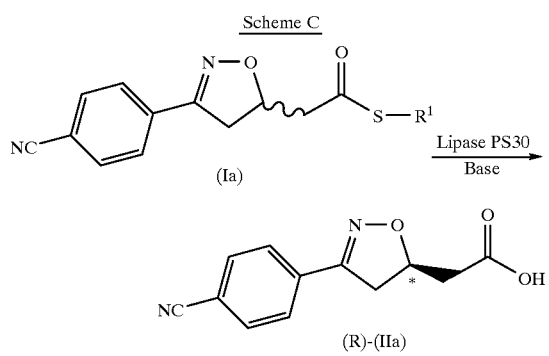

Scheme C

The invention combines two processes: racemization of a chiral center at the beta carbon to the thioester and the enzymatic hydrolysis of the thioester. This combination into a process of dynamic resolution constitutes the value of the invention. This invention discloses a method for the resolution of carboxylic acids substituted at the beta position with an isoxazoline ring. More preferably, this invention reveals a superior method to prepare compound (R)-(IIa), an important intermediate within the synthetic sequence to prepare compound (X).

The possibility to conduct enzymatic resolutions of racemic molecules and obtain a conversion in greater than 51% yield to optically pure product without the necessity of conducting a separate racemization step is of great potential value. This process saves time and money as it minimizes the number of reactions that must be run to obtain chiral product. This process decreases preparation times, reduce the cost of the product by minimizing the number of manipulations and reagents/solvents used, and increases the yield.

SUMMARY OF THE INVENTION

The instant invention provides novel processes for the resolution of stereoisomeric mixtures consisting of substituted isoxazolin-5-yl acetic acid, protected as a thioester, possessing a chiral center at the beta position of the carboxylic acid as part of the isoxazoline ring. This invention reveals a superior process to prepare compounds of formula (II) wherein enzymatic hydrolysis of a stereoisomeric mixture of compounds of formula (I) is coupled with racemization of (I) at the beta carbon to the thioester thus allowing greater than 80% conversion of a mixture of chiral isomers, such as compounds (I), into product (II) with optical purity greater than 90%. More specifically, this invention reveals a superior process to prepare compound (R)-(IIa), an important intermediate within the synthetic preparation of compound (X), wherein enzymatic hydrolysis of an enantiomeric mixture of compound (Ia) is coupled with racemization of compound (Ia) thus allowing greater than 85% conversion of a mixture of chiral isomers of compound (Ia) into product (R)-(IIa) with optical purity greater than 90%.

DETAILED DESCRIPTION OF THE INVENTION

The present invention provides methods for the preparation of substituted isoxazolin-5-yl acetic acid compounds of formula (R)-(II) or (S)-(II) in high optical purity from a stereoisomeric mixture of a thioester of a substituted isoxazolin-5-yl acetate. Such compounds are useful in the synthesis of compounds for pharmaceuticals, especially compound (X) and compounds in the treatment of thrombolytic disorders, and agricultural products.

[1] There is provided by this invention a process for the preparation of optically active compounds of formula (R)-(II) of (S)-(II):

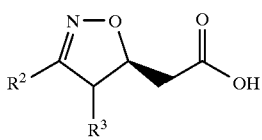

(R)-(II)

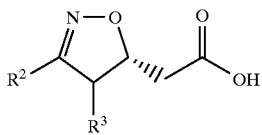

(S)-(II)

or a salt form thereof, wherein:

$R^2$ is —H, halo, —$CF_3$, —CN, —$NO_2$, —OH, $C_1$–$C_8$ alkoxy, $C_1$–$C_{10}$ alkylcarbonyl, —N($R^{12}$)$R^{13}$, —CHO, —$CO_2$H, —C(=O)$R^{5a}$, —CONR$^5$R$^{5a}$, —C(=NH)NR$^5$R$^{5a}$, —SR$^{5a}$, —$SO_2$R$^{5a}$, —$SO_2$NR$^5$R$^{5a}$, $C_1$–$C_8$ alkyl substituted with 0-3 $R^4$, $C_2$–$C_8$ alkenyl substituted with 0-3 $R^4$, $C_2$–$C_8$ alkynyl substituted with 0-2 $R^4$, $C_3$–$C_{10}$ cycloalkyl substituted with 0-3 $R^4$, $C_6$–$C_{10}$ aryl substituted with 0-3 $R^4$, a 5–10 membered heterocyclic ring containing 1–4 N, O, or S heteroatoms, wherein said heterocyclic ring may be saturated, partially saturated, or fully unsaturated, said heterocyclic ring being substituted with 0-2 $R^4$, an amino acid, or a peptide;

$R^3$ is hydrogen, $C_1$–$C_4$ alkyl substituted with 0-3 $R^4$, or phenyl substituted with 0-3 $R^4$;

$R^4$ is selected from H, $C_1$–$C_{10}$ alkyl, —OH, $C_1$–$C_{10}$ alkoxy, —$NO_2$, $C_1$–$C_{10}$ alkylcarbonyl, —N($R^{12}$)$R^{13}$, —CN, halo, —$CF_3$, —CHO, —$CO_2$H, —C(=O)$R^{5a}$, —CONR$^5$R$^{5a}$, —C(=NH)NR$^5$R$^{5a}$, —OC(=O)$R^{5a}$, —OR$^{5a}$, —OC(=O)NR$^5$R$^{5a}$, —OCH$_2$CO$_2$H, —CO$_2$CH$_2$CO$_2$H, —NR$^{5a}$C(=O)R$^{5a}$, —NR$^{5a}$C(=O)OH, —NR$^{5a}$C(=O)NR$^5$R$^{5a}$a, —NR$^{5a}$SO$_2$NR$^5$R$^{5a}$a, —NR$^{5a}$SO$_2$R$^5$, —SR$^{5a}$, —SO$_2$R$^{5a}$, —SO$_2$NR$^5$R$^{5a}$, $C_2$–$C_6$ alkenyl, $C_3$–$C_{11}$ cycloalkyl, $C_4$–$C_{11}$ cycloalkylmethyl or $C_6$–$C_{10}$ aryl optionally substituted with 1–3 groups selected from halogen, $C_1$–$C_4$ alkoxy, $C_1$–$C_4$ alkyl, —$CF_3$, —S(O)$_2$Me, or —NMe$_2$;

$R^5$ is selected from H, $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0-2 $R^6$;

$R^{5a}$ is selected from H, $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0-2 $R^6$;

alternately, $R^5$ and $R^{5a}$ can be taken together to be 3-azabicyclononyl, 1-piperidinyl, 1-morpholinyl or 1-piperazinyl, each being optionally substituted with $C_1$–$C_6$ alkyl, $C_6$–$C_{10}$ aryl, $C_7$–$C_{11}$ arylalkyl, $C_1$–$C_6$ alkylcarbonyl, $C_3$–$C_7$ cycloalkylcarbonyl, $C_1$–$C_6$ alkylsulfonyl or $C_6$–$C_{10}$ arylsulfonyl;

$R^6$ is selected from H, $C_1$–$C_{10}$ alkyl, hydroxy, $C_1$–$C_{10}$ alkoxy, nitro, $C_1$–$C_{10}$ alkylcarbonyl, or —N($R^{12}$)$R^{13}$;

$R^{12}$ and $R^{13}$ are independently selected from H, methyl, or ethyl;

said process comprising:

contacting, in a suitable solvent, a stereoisomeric mixture of a compound of Formula (I)

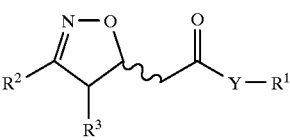

(I)

wherein:

Y is S;

$R^1$ is —C($R^{10}$)$_2$($R^{10a}$),
—C($R^{10}$)$_2$—C($R^{10b}$)$_2$($R^{10c}$),
—C($R^{10}$)$_2$—C($R^{10b}$)$_2$—C($R^{10c}$)$_3$,
—C($R^{10}$)$_2$—C($R^{10b}$)=C($R^c$)$_2$,
—C($R^{10}$)$_2$—C≡C($R^{10c}$),
—C($R^{10}$)=C($R^{10b}$) ($R^{10c}$),
—C($R^{10}$)=C($R^{10b}$)—C($R^{10c}$)$_3$,
—C≡C($R^{10c}$),
—C≡C—C($R^{10c}$)$_3$, $R^{10}$ is H or F;

$R^{10a}$ is selected from H, F, Cl, Br, —CH$_3$, —CH$_2$CH$_3$, —CH$_2$CH$_2$CH$_3$, —CF$_3$, —CF$_2$CF$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, and cyclopropyl;

$R^{10b}$ is H, F, Cl, or Br;

$R^{10c}$ at each occurrence is, independently, selected from H, halo, $C_1$–$C_3$ haloalkyl, —OH, $C_1$–$C_4$ alkoxy, —CF$_3$, —SCH$_3$, —SCH$_2$CH$_3$, —SCH$_2$CH$_2$CH$_3$, —CN, —NO$_2$, —S(O)$_2$Me, —NMe$_2$, $C_1$–$C_6$ alkyl substituted with 0-3 $R^{11}$, $C_2$–$C_6$ alkenyl substituted with 0-3 $R^{11}$, $C_2$–$C_6$ alkynyl substituted with 0-2 $R^{11}$, $C_3$–$C_6$ cycloalkyl substituted with 0-3 $R^{11}$, $C_6$–$C_{10}$ aryl substituted with 0-3 $R^{11}$, or $C_4$–$C_{10}$ heterocycle substituted with 0-3 $R^{11}$; and $R^{11}$ is selected from the group H, halo, $C_1$–$C_4$ alkyl, $C_1$–$C_3$ haloalkyl, $C_1$–$C_4$ alkoxy, phenyl, —OH, —NO$_2$, —CN, —CF$_3$, —S(O)$_2$Me, and —NMe$_2$;

with a suitable lipase in the presence of a racemization agent, while maintaining a suitable basic pH by addition of a base or an acid, to form a compound of formula (R)-(II) or formula (S)-(II) in greater than 51% yield and greater than 80% optical purity.

[2] In a preferred embodiment the instant invention provides a process for the preparation of compounds of Formula (R)-(II):

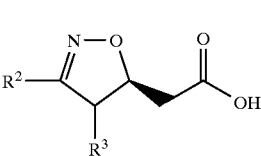

(R)-(II)

or a salt form thereof, wherein:

$R^2$ is phenyl substituted with 0-3 $R^4$, $R^3$ is hydrogen;

$R^4$ is selected from H, $C_1$–$C_{10}$ alkyl, —OH, $C_1$–$C_{10}$ alkoxy, —NO$_2$, $C_1$–$C_{10}$ alkylcarbonyl, —N($R^{12}$)$R^{13}$, —CN, halo, —CF$_3$, —CHO, —CO$_2$H, —C(=O)$R^{5a}$, —CONR$^5$R$^{5a}$, —C(=NH)NR$^5$R$^{5a}$, —OC(=O)$R^{5a}$, OR$^{5a}$, —OC(=O)NR$^5$R$^{5a}$, —OCH$_2$CO$_2$H, —CO$_2$CH$_2$CO$_2$H, —NR$^{5a}$C(=O)R$^{5a}$, —NR$^{5a}$C(=O)OH, —NR$^{5a}$C(=O)NR$^5$R$^{5a}$, —NR$^{5a}$SO$_2$NR$^5$R$^{5a}$, —NR$^{5a}$SO$_2$R$^5$, —SO$_2$R$^{5a}$, —SO$_2$NR$^5$R$^{5a}$, C$_2$–C$_6$ alkenyl, C$_3$–C$_{11}$ cycloalkyl, C$_4$–C$_{11}$ cycloalkylmethyl or
C$_6$–C$_{10}$ aryl optionally substituted with 1–3 groups selected from halogen, C$_1$–C$_4$ alkoxy, C$_1$–C$_4$ alkyl, —CF$_3$, —S(O)$_2$Me, or —NMe$_2$;
R$^5$ is selected from H, C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0-2 R$^6$;
R$^{5a}$ is selected from H, C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0-2 R$^6$;
alternately, R$^5$ and R$^{5a}$ can be taken together to be 3-azabicyclononyl, 1-piperidinyl, 1-morpholinyl or 1-piperazinyl, each being optionally substituted with C$_1$–C$_6$ alkyl, C$_6$–C$_{10}$ aryl, C$_7$–C$_{11}$ arylalkyl, C$_1$–C$_6$ alkylcarbonyl, C$_3$–C$_7$ cycloalkylcarbonyl, C$_1$–C$_6$ alkylsulfonyl or C$_6$–C$_{10}$ arylsulfonyl;
R$^6$ is selected from H, C$_1$–C$_{10}$ alkyl, hydroxy, C$_1$–C$_{10}$ alkoxy, nitro, C$_1$–C$_{10}$ alkylcarbonyl, or —N(R$^{12}$)R$^{13}$;
R$^{12}$ and R$^{13}$ are independently selected from H, methyl, or ethyl;
said process comprising:
contacting, in a suitable solvent, a stereoisomeric mixture of a compound of Formula (I):

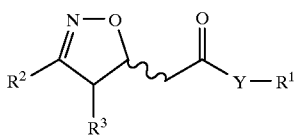

(I)

wherein:
Y is S;
R$^1$ is —C(R$^{10}$)$_2$(R$^{10a}$),
 —C(R$^{10}$)$_2$—C(R$^{10b}$)$_2$(R$^{10c}$),
 —C(R$^{10}$)$_2$—C(R$^{10b}$)$_2$—C(R$^{10c}$)$_3$,
 —C(R$^{10}$)$_2$—C(R$^{10b}$)=C(R$^{10c}$)$_2$,
 —C(R$^{10}$)$_2$—C≡C(R$^{10c}$),
 —C(R$^{10}$)=C(R$^{10b}$) (R$^{10c}$),
 —C(R$^{10}$)=C(R$^{10b}$)—C(R$^{10c}$)$_3$,
 —C≡C(R$^{10c}$),
 —C≡C—C(R$^{10c}$)$_3$,
R$_{10}$ is H or F;
R$^{10a}$ is selected from H, F, Cl, Br, —CH$_3$, —CH$_2$CH$_3$, —CH$_2$CH$_2$CH$_3$, —CF$_3$, —CF$_2$CF$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, and cyclopropyl;
R$^{10b}$ is H, F, Cl, or Br;
R$^{10c}$ at each occurrence is, independently, selected from H, halo, C$_1$–C$_3$ haloalkyl, —OH, C$_1$–C$_4$ alkoxy, —CF$_3$, —SCH$_3$, —SCH$_2$CH$_3$, —SCH$_2$CH$_2$CH$_3$, —NMe$_2$,
C$_1$–C$_6$ alkyl substituted with 0-3 R$^{11}$,
C$_2$–C$_6$ alkenyl substituted with 0-3 R$^{11}$,
C$_2$–C$_6$ alkynyl substituted with 0-2 R$^{11}$,
C$_3$–C$_6$ cycloalkyl substituted with 0-3 R$^{11}$,
C$_6$–C$_{10}$ aryl substituted with 0-3 R$^{11}$, or
C$_4$–C$_{10}$ heterocycle substituted with 0-3 R$^{11}$; and
R$^{11}$ is selected from the group H, halo, C$_1$–C$_4$ alkyl, C$_1$–C$_3$ haloalkyl, C$_1$–C$_4$ alkoxy, phenyl, —OH, —NO$_2$, —CN, —CF$_3$, —S(O)$_2$Me, and —NMe$_2$;
with a suitable lipase in the presence of a racemization agent, while maintaining a suitable basic pH by addition of a base or an acid, to form a compound of formula (R)-(II) in greater than 51% yield and greater than 80% optical purity.

[3] In a more preferred embodiment the instant invention provides a process for the preparation of a compound of Formula (R)-(IIa):

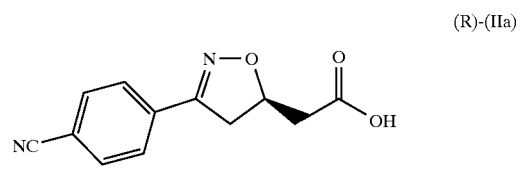

(R)-(IIa)

or a salt form thereof, said process comprising:
contacting, in a suitable solvent, a stereoisomeric mixture of a compound of Formula (Ia):

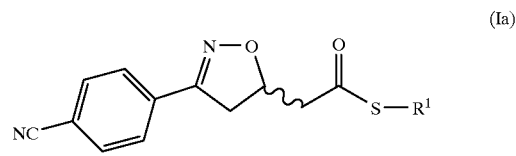

(Ia)

wherein:
R$^1$ is —CH$_2$(R$^{10a}$),
 —CH$_2$—CH$_2$(R$^{10c}$),
 —CH$_2$—CH$_2$—C(R$^{10c}$)$_3$,
 —CH$_2$—CH=C(R$^{10c}$)$_2$,
 —CH$_2$—C≡C(R$^{10c}$),
R$^{10a}$ is selected from H, —CH$_3$, —CH$_2$CH$_3$, and —CH$_2$CH$_2$CH$_3$; R$^{10c}$ at each occurrence is, independently, selected from H, —OH, C$_1$–C$_4$ alkoxy, —NMe$_2$,
C$_1$–C$_6$ alkyl substituted with 0-3 R$^{11}$,
C$_2$–C$_6$ alkenyl substituted with 0-3 R$^{11}$,
C$_2$–C$_6$ alkynyl substituted with 0-2 R$^{11}$, or
C$_3$–C$_6$ cycloalkyl substituted with 0-3 R$^{11}$; and
R$^{11}$ is selected from the group H, halo, C$_1$–C$_4$ alkyl, C$_1$–C$_3$ haloalkyl, C$_1$–C$_4$ alkoxy, —OH, —NO$_2$, —CN, —CF$_3$, —S(O)$_2$Me, and —NMe$_2$;
with a suitable lipase in the presence of a racemization agent, while maintaining a suitable basic pH by addition of a base or an acid, to form a compound of formula (R)-(IIa) in greater than 51% yield and greater than 80% optical purity.

[23] In an even more preferred embodiment the instant invention provides a process for the preparation of a compound of (R)-(IIa):

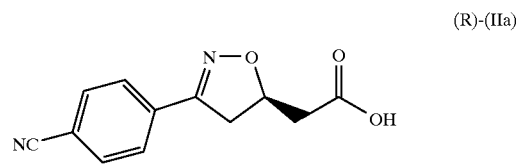

(R)-(IIa)

or a salt form thereof, said process comprising:
contacting, in water, a stereoisomeric mixture of a compound of Formula (Ia):

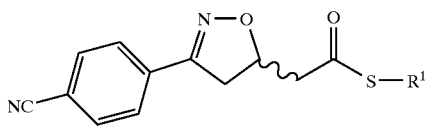

(Ia)

wherein R¹ is ethyl, n-propyl or n-butyl,
with the lipase Amano PS30 in the presence of racemization agent trimethylamine, while maintaining a suitable pH in the range of about 8.0 to about 10.0 by addition of a base or an acid, to form a compound of formula (R)-(IIa) in greater than 51% yield and greater than 80% optical purity.

[8] In a second embodiment the instant invention provides a process for the preparation of a compound of Formula (R)-(IIa) as described in the first embodiment further comprising a suitable buffer added to the suitable solvent to assist in maintaining the suitable pH by addition of a base.

[13] In a more preferred second embodiment the instant invention provides a process for the preparation of a compound of Formula (R)-(IIa), or a salt form thereof, wherein said process comprises:
contacting, in water, in which is dissolved a suitable buffer, a stereoisomeric mixture of a compound of Formula (Ia):

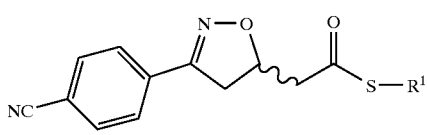

(Ia)

wherein R¹ is n-propyl;
with the lipase Amano PS30 in the presence of racemization agent trimethylamine, while maintaining a suitable pH in the range of about 8.0 to about 10.0 by addition of a base or an acid, to form a compound of formula (R)-(IIa) in greater than 51% yield and greater than 80% optical purity.

[14] In a third embodiment the instant invention provides a process for the preparation of a compound of Formula (R)-(IIa) as described in the first embodiment further comprising a suitable nonionic, cationic or anionic surfactant added to the suitable solvent.

[20] In a more preferred third embodiment the instant invention provides a process for the preparation of a compound of Formula (R)-(IIa), or a salt form thereof, wherein said process comprises:
contacting, in water, in which is dissolved a suitable nonionic, cationic or anionic surfactant, a stereoisomeric mixture of a compound of Formula (Ia):

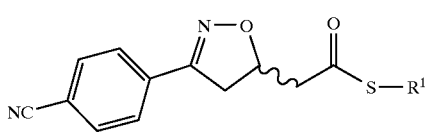

(Ia)

wherein R¹ is n-propyl,
with the lipase Amano PS30 in the presence of racemization agent trimethylamine, while maintaining a suitable pH in the range of about 8.0 to about 10.0 by addition of a base or an acid, to form a compound of formula (R)-(IIa) in greater than 51% yield and greater than 80% optical purity.

[24] In a fourth embodiment the instant invention provides a process for the preparation of a compound of (R)-(IIa) as described in the first embodiment further comprising a suitable buffer added to the suitable solvent to assist in maintaining the suitable pH by addition of a base and a suitable nonionic, cationic or anionic surfactant added to the suitable solvent.

[25] In an more preferred fourth embodiment the instant invention provides a process for the preparation of a compound of Formula (R)-(IIa), or a salt form thereof, wherein said process comprises:
contacting, in water, in which is dissolved a suitable buffer and a suitable nonionic, cationic or anionic surfactant, a stereoisomeric mixture of a compound of Formula (Ia):

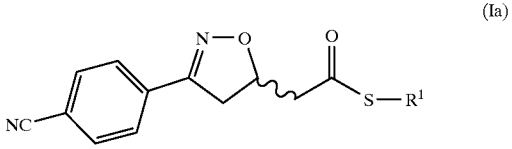

(Ia)

wherein R¹ is n-propyl,
with the lipase Amano PS30 in the presence of racemization agent trimethylamine, while maintaining a suitable pH in the range of about 8.0 to about 10.0 by addition of a base, to form a compound of formula (R)-(IIa) in greater than 51% yield and greater than 80% optical purity.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. The amidine compounds described herein may exist as tautomeric forms, and all such stable tautomers are included in the present invention. It will be appreciated that compounds of the present invention may contain, in addition to the chiral center beta to the thioester in compounds of formula (I), asymmetrically substituted carbon atoms and may be isolated in optically active or racemic forms. All chiral, diastereomeric, racemic forms and all geometric isomeric forms of a structure are intended, unless the specific stereochemistry or isomer form is specifically indicated.

As used herein, the term "stereoisomeric mixture" is intended to mean a mixture of optically active compounds, said optically active compounds can have one or more chiral centers, for example enantiomers or diastereomers. However, the term stereoisomeric mixture denotes a mixture of optically active compounds having equal (racemic) or non-equal amounts of optically active compounds in relation to the chiral center at the beta carbon of a thioester of a substituted isoxazolin-5-yl acetate, as depicted in compounds of formula (I).

When any variable occurs more than one time in any constituent or in any formula, its definition on each occurrence is independent of its definition at every other occurrence.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms; for example, "$C_1$–$C_8$" denotes alkyl having 1 to 8 carbon atoms, ie. methyl, ethyl, n-propyl, i-propyl, n-butyl, i-butyl, s-butyl, t-butyl, pentyl, hexyl, septyl, octyl, and branched isomers therin. "Haloalkyl" is intended to include both branched and straight-chain saturated aliphatic hydrocarbon groups having the specified number of carbon atoms, substituted with 1 or more halogen (for example -$C_vF_w$, where v=1 to 3 and w=1 to (2v+1)); "alkoxy" represents an alkyl group of indicated number of carbon atoms attached through an oxygen bridge. "Alkylcarbonyl" is intended to include an alkyl group of an indicated number of carbon atoms attached through a carbonyl group to the residue of the compound at the designated location. "Alkylsulphonyl" is intended to include an alkyl group of an indicated number of carbon atoms attached through a sulphonyl group (—$SO_2$—) to the residue of the compound at the designated location.

"Cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. The term "cycloalkylalkyl" represents a cycloalkyl group attached through an alkyl bridge; for example cyclopropylmethyl, cyclopropylethyl, cyclobutylmethyl, cyclopentylmethyl, cyclohexylmethyl, and so forth. "Cycloalkylcarbonyl" is intended to include a cycloalkyl group of an indicated number of carbon atoms attached through a carbonyl group to the residue of the compound at the designated location.

"Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge; for example benzyl, phenylethyl, and phenylpropyl. "Arylcarbonyl" is intended to include an aryl group of an indicated number of carbon atoms attached through a carbonyl group to the residue of the compound at the designated location. "Arylsulphonyl" is intended to include an aryl group of an indicated number of carbon atoms attached through a sulphonyl group (—$SO_2$—) to the residue of the compound at the designated location.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4H-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl.

The reactions of the synthetic methods claimed herein are preferably carried out in the presence of a suitable base, said suitable base being any of a variety of bases, the presence of which in the reaction facilitates the synthesis of the desired product. Suitable bases may be selected by one of skill in the art of organic synthesis. Suitable bases include, but are not limited to, inorganic bases such as alkali metal, alkali earth metal, thallium, and ammonium hydroxides, alkoxides, phosphates, and carbonates, such as sodium hydroxide, potassium hydroxide, sodium carbonate, potassium carbonate, cesium carbonate, thallium hydroxide, thallium carbonate, tetra-n-butylammonium carbonate, and ammonium hydroxide. Suitable bases also include organic bases, including but not limited to aliphatic amines, such as trialkyl amines, dialkyl amines and monoalkyl amines, N,N-diisopropylethylamine, N,N-diethylcyclohexylamine, N,N-dimethylcyclohexylamine, N,N,N'-triethylenediamine, N,N-dimethyloctylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), and tetramethylethylenediamine (TMEDA); and aromatic amines, such as pyridine and substituted pyridines such as N,N-dimethylaminopyridine (DMAP), 4-pyrrolidinopyridine, 4-piperidinopyridine.

As used herein, the term racemization agent is intended to mean any base sufficiently strong enough to enable the rate of racemization of the chiral center designated as the beta carbon in compounds of formula (I) to match or exceed the rate of enzyme hydrolysis. Examples of racemization agents include, but are not limited to, trimethylamine, triethylamine, tripropylamine, tributylamine, trioctylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); pyridine and substituted pyridines such as N,N-dimethylaminopyridine (DMAP), 4-pyrrolidinopyridine, and 4-piperidinopyridine.

The reactions of the synthetic methods claimed herein may be carried out by the addition of a suitable acid in order to establish or maintain a suitable basic pH especially in the absence of a buffer, said suitable acid being any of a variety of acids, the presence of which in the reaction facilitates the synthesis of the desired product. Suitable acids may be selected by one of skill in the art of organic synthesis. Suitable acids include, but are not limited to, organic acids, such as acetic acid, and inorganic acids such as HCl, HBr and $H_3PO_4$.

As used herein, the term "hydrolase" or "lipase" is intended to mean any enzyme capable of hydrolyzing compounds of formula (I), containing thioesters of a substituted isoxazolin-5-yl acetate, to their corresponding substituted isoxazolin-5-yl carboxylic acids. Additionally, the "hydrolase" or "lipase" is selective for compounds containing chiral centers beta to the thioester as described in compounds of formula (I). In being selective for one chiral center of a stereoisomeric mixture, it is intended that the lipase may select either the (R) enantiomer or the (S) enantiomer beta to the thioester as described in compounds of formula (I). Additionally, the hydrolase or lipase may be homogeneous in solution with the substrates of compounds of formula (I) or it may be heterogeneous in solution, for example immobilized on an inert insoluble material. The hydrolase or lipase may be in lyophilisate, spray-dried or heat-dried form as well as suspended or immobilized form.

Examples of enzymes capable of hydrolyzing compounds of formula (I) in the process of the invention can include microbial and bacterial hydrolases or lipases of the Candida, Pseudomonas, Mucor, Rhizopus, Aspergillus, Bacillus, Streptomyces, Geotrichum, and Chromobacterium genus as well as enzymes derived from animal tissue.

Examples of commercially available hydrolases or lipases suitable for use in the present invention include, but are not limited to, Amano AX (Pseudomonas sp.), Amano PS30 (Pseudomonas sp.), Amano FAP (*Rhizopus javanicus*), Amano AY 30 (*Candida cylindracea*), Amano L (*Candida lipolytica*), Amano AP12 (*Aspergillus niger*), Amano protease N (*Bacillus subtilis*), chymotrypsin, subtilisin, thermitase (*Thermoactinimyces vulgaris*), acetylchloline esterase, electric eel acetylcholine esterase, pig liver esterase, cholesterol esterase, procine pancreatic lipase, rabbit liver esterease, and hydrolases derived from *Geotrichum candidum, Rhizopus nigricans, Rhizopus oryzae, Aspergillus oryzae, Streptomyces griseus, Streptomyces griseus, Aspergillus saitoi, Aspergillus niger, Mucor miehei*, and *Chromobacterium viscosum*.

As used herein, the term "dynamic resolution" is intended to mean a process under conditions wherein a stereoisomer of a stereoisomeric mixture is selected by an enzyme and hydrolyzed, preferentially, over its optical isomer while the optical isomer is simultaneously racemized into the enzyme selected stereoisomer. Performing the resolution reaction under such conditions allows greater than 51% conversion of a starting material of a stereoisomeric mixture into one stereoisomeric product with optical purity greater than 80%.

For example, a stereoisomeric mixture of racemates would produce the (R) isomer product in greater than 51% yield with greater than 80% optical purity while the (S) isomer reactant racemizes into the (R) isomer reactant. Essentially, racimerization is coupled with enzymatic resolution.

As used herein, the term "optical purity" or "enantiomeric purity" is intended to refer only to the chiral center that is being resolved by the invention and is measured as the mole percent of isomeric (R) or (S) product verses the total moles of isomeric (R) and (S) product. For example, and without limitation, an optical purity of 80% for a compound of formula (R)-(II) means the (R)-(II) isomer is in 80% yield with a 20% yield of the (S)-(II) isomer.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected. A given reaction may also be carried out in a biphasic system wherein the racemization of the substrates of interest occur.

Suitable halogenated solvents include: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, anisole, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable basic solvents include: 2-, 3-, or 4-picoline, pyrrole, pyrrolidine, morpholine, pyridine, or piperidine.

Suitable hydrocarbon solvents include: benzene, cyclohexane, pentane, hexane, toluene, cycloheptane, methylcyclohexane, heptane, ethylbenzene, m-, o-, or p-xylene, octane, indane, nonane, or naphthalene.

As used herein, "suitable solvent" is intended to include water and mixtures of water with an organic solvent wherein the organic solvent can be a suitable halogenated solvent, suitable ether solvent, suitable protic solvent, suitable aprotic solvent, suitable basic solvent or a suitable hydrocarbon solvent. When mixtures of water and an organic solvent are used the organic solvent is preferably acetonitrile, toluene, xylene, ether or an alcohol, such as, methanol, ethanol, n-propanol or isopropanol, n-butanol, sec-butanol, tert-butanol. When organic solvents are used the total composition of organic solvents in the mixture can range from 0–50% for alcohols and 0–95% for non-alcohols. The solvent mixture may be biphasic to faciliate the reaction of compounds of formula (I).

As used herein, the term "buffer" is intended to include a conjugate acid/base pair which when dissolved into a suitable solvent assist in resisting changes in pH of the suitable solvent due to additions of acids or bases or dilution. Conjugate acid/base pairs capable of perfoming as suitable buffers in the pH range of about 8 to about 11 can be prepared by one skilled in the art from compounds which include, but are not limited to, carbonate salts, such as $Na_2CO_3$, $K_2CO_3$, $NaHCO_3$, and $KHCO_3$; phosphate salts, such as $Na_3PO_4$, $Na_2HPO_4$, $NaH_2PO_4$, $K_3PO_4$, $K_2HPO_4$, and $KH_2PO_4$; borate salts, sodium 5,5-diethylbarbiturate, glycylglycine, ethanolamine, diethanolamine, 2,5-dimethylimidazole, pyrophosphoric acid, tris(hydroxymethyl)aminomethane, N-((trishydroxymethyl)methyl)glycine, 4-(2-hydroxyethyl)-1-piperazinepropanesulfonic acid, 2-amino-2-methyl-1,3-propanediol, 2-amino-2-ethyl-1,3-propanediol, 2-amino-2-methyl-1-propanol, N,N-(bis-2-hydroxymethyl)glycine, glycine, 2-(cyclohexylamino)ethane-sulfonic acid, trimethylamine, and ethylendiamine.

As used herein, the term "surfactant" is intended to include anionic, cationic and nonionic surface active agents. Examples of suitable surfactants include, but are not limited to, bile salts, dioctyl sodium sulphosuccinate, diosgenin, sarkosyl, sodium dodecyl sulphate, cetyl pyridinium chloride, cetyl trimethyl ammonium bromide, 3-[(3-cholamidopropyl)-dimethylammonio]-1-propanesulphonate, N,N-dimethyldodecyl-amino-N-oxide, octylglucoside, polyoxyethylene(PEG) alcohols such as PEG(23) lauryl alcohol, PEG(10) cetyl alcohol, PEG(20) cetyl alcohol, PEG(9–10) lauryl-myristyl alcohol, and PEG (17) cetyl-stearyl alcohol; and compounds popularly known as phase transfer agents such as benzyltrimethylammonium chloride and tricaprylylmethylammonium chloride. Additional examples of suitable surfactants include, but are not limited to, polyoxyethylene(PEG) compounds such as PEG-p-t-octylphenol derivatives such as Triton® X-45 (PEG(5) p-t-octylphenol), Triton® X-114 (PEG(7–8)p-t-octylphenol), Triton® X-100 (PEG(9–10)p-t-octylphenol), Triton® X-102 (PEG(12–13)p-t-octylphenol), Triton® X-165 (PEG(16)p-t-octylphenol), Triton® X-305 (PEG(30) p-t-octylphenol) and PEG(9)-p-t-octylphenol; PEG(9–10) nonylphenol known as Triton® N-101; PEG sorbitol esters known as Tween® 20, Tween® 40, Tween® 60, and Tween® 80; polyoxypropylene-PEG-esters known as Pluronic® L62, PluronicO L64, and Pluronic® L68; and Triton® A 20.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl) cyclohexanecarboxylic acid, 2-, 3-, and 4-(aminomethyl) benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Synthesis

It is the object of the present invention to provide processes for the dynamic resolution of stereoisomeric mixtures of substituted isoxazolines which are useful in the synthesis of pharmaceuticals, such as compound (X). The methods of the present invention, by way of example and without limitation, may be further understood by reference to Scheme 1. Scheme 1 details the general one pot process for the dynamic resolution of a substituted isoxazolin-5-yl acetate thioester wherein Y is sulfur and the chiral center to be resolved is the beta carbon from the thioester carbonyl group. Although the (R) stereoisomer is shown as the product of Scheme 1, alternatively it is equally possible to obtain the (S) stereoisomer depending on the choice of lipase or hydrolase used in the process. The (S) stereoisomer has been described above as compounds of formula (S)-(II).

Scheme 1

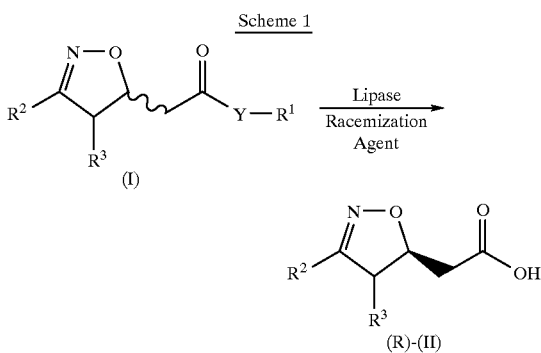

Scheme 1 comprises the enzymatic resolution of a stereoisomeric mixture of compounds of formula (I) to compounds of formula (R)-(II) or salt forms therof. The resolution of compounds of formula (I), ie simultaneous racemization and hydrolysis, is conducted in one pot by contacting compounds of formula (I) with a suitable lipase or hydrolase and a racemization agent under basic pH conditions. Additionally, the one pot process may include a buffer to assist in the maintenance of basic pH and/or a surfactant.

This step is conducted by reacting a stereoisomeric mixture of a compound of formula (I) in a suitable solvent, in which a suitable buffer and/or a suitable surfactant may or may not be dissolved, with a suitable lipase or hydrolase and a racemization agent, followed by addition of a suitable base or acid to maintain a basic pH. The order of addition is not determinative other than the pH must be maintained by addition of base in order for racemization to proceed. By way of general guidance, the process is conducted by: a) charging a solution with a suitable buffer, a suitable racemization agent, a suitable surfactant and a base or an acid; b) charging the solution with a stereoisomeric mixture of a compound of formula (I); c) charging the solution with a suitable lipase or hydrolase; d) maintaining the pH in the range of about 8.0 to about 11.0; and e) monitoring the process for a sufficient amount of time until the resolution process is complete. Compounds of formula (R)-(II) may be separated from solution by standard methods of work up; an example of which is shown in Example 18. By general guidance the final solution is filtered to remove heterogenous solids if present and not the product followed by acidification of the filtrate to a pH of about 1.0 to about 4.0 to precipitate the compounds of formula (R)-(II). Heterogenous solids are present if the starting materials are not appreciably soluble in the solvent, if the lipase or hydrolase is immobilized on an inert insoluble material, or if other insoluble filtration materials known to one skilled in the art have been added as part of the work up. Generally, it is preferred that the product compounds (R)-(II) remain soluble in the solvent as a salt form of the carboxylate species until acidification upon workup.

By way of general guidance, maintaining the pH in the range of about 8.0 to about 11.0 can be conducted by any method known to one skilled in the art of chemical synthesis. Such methods include, but are not limited to, addition of base by automatic titrators, by mechanical addition or by manual addition.

Preferred suitable solvents are water and mixtures of water with an organic solvent. When mixtures of water and an organic solvent are used the organic solvent can be acetonitrile, toluene, xylene, ether or an alcohol, such as, methanol, ethanol, n-propanol and isopropanol. When organic solvents are used the total composition of organic solvents in the mixture can range from 0–95% unless the organic solvent is an alcohol, wherein the solvent mixture can range from 0–50%, preferably. When organic solvents are used the process can be a biphasic solution.

The scope of thioester groups known to one skilled in the art that would function efficiently to produce compound (R)-(IIa) is diverse. In a broad sense, any thioester group that possesses sufficient electron withdrawing ability to permit a reasonable rate of racemization at the beta carbon is acceptable.

In the process of Scheme 1 the chemical yield of compounds of formula (R)-(II) can range from 51–100%, wherein the preferable yield is 75–100% and a more preferable yield is about 80% to 100%. In addition to chemical yield, the optical purity of compounds of formula (R)-(II) can range from 51–100%; wherein the preferable optical purity is 80–100%; a more preferable optical purity is about 90% to 100%; and a most preferable optical purity is about 95% to 100%.

The present invention, by way of example and without limitation, may be further exemplified in the preparation of compound (R)-(IIa), or salt forms thereof, by reference to Scheme 2.

Scheme 2

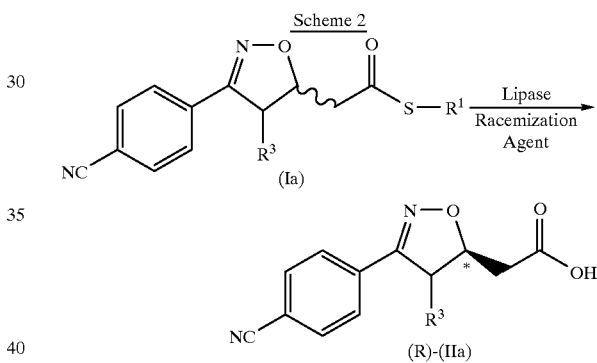

This step is conducted by reacting a mixture of enantiomers of a compound of formula (Ia) in a suitable solvent, in which a suitable buffer and/or a suitable surfactant may or may not be dissolved, with a suitable lipase or hydrolase and a racemization agent, followed by addition of a suitable base or acid to maintain a basic pH. The order of addition is not determinative other than the pH must be maintained by addition of base in order for the racemization to proceed. For example, a lipase or hydrolase may be added to the reaction before compound (Ia) or the racemization agent, as long as all of the above are contacted with each other before additional base is added to maintain the basic pH of the process. The buffer or surfactant, if added, can be added at any time.

The process is conducted under aerobic or anaerobic atmosphere, for example open air, nitrogen or argon.

By way of general guidance, the process is conducted by: a) charging a solution with a suitable buffer, a suitable racemization agent, a suitable surfactant and a base or an acid; b) charging the solution with a stereoisomeric mixture of a compound of formula (I); c) charging the solution with a suitable lipase; d) maintaining the pH in the range of about 8.0 to about 11.0; and e) monitoring the process for a sufficient amount of time until the resolution process is complete. Compound (R)-(IIa) may be separated from solution by standard methods of work up; an example of which is shown in Example 18. By general guidance the final solution is filtered to remove heterogenous solids followed by acidification of the filtrate to a pH of about 1.0 to about 4.0 to precipitate compound (R)-(IIa).

Preferred suitable solvents are water and mixtures of water with acetonitrile, toluene, xylene, ether, methanol, ethanol, n-propanol or isopropanol. When organic solvents are used the total composition of organic solvents in the mixture can range from 0–50% for alcohols and 0–95% for non-alcohols. A most preferred suitable solvent is water.

Preferred pH range for this process is about 8.0 to about 11.0. More preferably the pH range is about 8.5 to about 10.0. Most preferably the pH range is about 8.5 to about 9.5.

The buffer may or may not be present and when present is readily chosen by one skilled in the art. Preferred suitable compounds for the preparation of the buffer for this process are sodium or potassium dihydrogen phosphate.

A preferred suitable surfactant is Triton® X-100, known as PEG(9–10)p-t-octylphenol, in the range of 0 grams to about 1 gram Triton® X-100 for every 5 grams of compounds of formula (I).

Preferred suitable lipases or hydrolases for this process are commercial enzymes purchased from a commercial source and used without further purification, examples of which are Amano PS30 and Amano AK. Most preferred is Amano PS30.

Preferred suitable racemization agents for this process are trimethylamine and triethylamine. Most preferred is trimethylamine. The preferred concentration range of suitable racemization agents for this process is about 0.5 equivalents to about 10 equivalents of racemization agent to equivalent of substrate; more preferred is 2 equivalents of racemization agent to equivalent of substrate.

Preferred bases for this process are sodium hydroxide and potassium hydroxide.

A preferred temperature range for this process is about 30° to about 60° C. More preferred is about 35° to about 50° C. Most preferred is about 38° to about 43° C.

The concentration ratio of weight enzyme, as commercially provided, to weight substrate can range from about 1:1 to about 1:500. A preferred concentration ratio of weight enzyme, as commercially provided, to weight substrate is 1:100; more preferred is 1:20; most preferred is 1:10. This ratio is affected by the percentage of active enzyme contained in the commercial preparation.

The preferred reaction time is an element dependent upon concentration of the reactants, temperature, pH, and yield to be achieved. Generally, a reaction time of 10 to 150 hours is achievable wherein about 30 to about 40 hours is preferred.

In the process of Scheme 2 the chemical yield of compound (R)-(IIa) can range from 51–100%, wherein the preferable yield is 75–100% and a more preferable yield is about 80% to 100%. In addition to chemical yield, the optical purity of compound (R)-(IIa) can range from 51–100%; wherein the preferable optical purity is 80–100%; a more preferable optical purity is about 90% to 100%; and a most preferable optical purity is about 95% to 100%.

A preferred atmosphere for this process is nitrogen.

Examples of agitation for this process can be, but are not limited to, physical or mechanical stirring, mixing, purging with a nonreactive gas or rotation of the reactor vessel. A preferred method of agitation is stirring.

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The following abbreviations are used herein:
DMF: N,N-dimethylformamide,
DBU: 1,8-diazabicyclo[5.4.0]undec-7-ene,
EtOH: ethyl alcohol,
NaOTMS: sodium trimethylsilanolate,
NCS: N-chlorosuccinimide,
pyr: pyridine,
TEA: triethylamine, and
THF: tetrahydrofuran.

Synthesis of the compounds of this invention relies on the dipolar cycloaddition of nitrile oxides with an appropriate dipolarophile as the key step (for reviews of 1,3-dipolar cycloaddition chemistry, see 1,3-Dipolar Cycloaddition Chemistry (Padwa, ed.), Wiley, New York, 1984; Kanemasa and Tsuge, *Heterocycles* 1990, 30, 719). Scheme 3 describes one synthetic sequence to compound (Ia) and adaptable to compounds of formula (I) of this invention. An appropriately substituted hydroxylamine is treated with NCS in DMF according to the method of Liu, et. al. (*J. Org. Chem.* 1980, 45, 3916). The resulting hydroximinoyl chloride is then dehydrohalogenated in situ using triethylamine to give a nitrile oxide, which undergoes a 1,3-dipolar cycloaddition to a suitably substituted alkene to afford the isoxazoline. Alternatively, the oxime may be oxidatively chlorinated, dehydrochlorinated and the resulting nitrile oxide trapped by a suitable alkene under phase transfer conditions according to the method of Lee (*Synthesis* 1982, 508). Intermediates containing alkali-sensitive functionality, such as nitrile, may be deesterified with excellent chemoselectivity using sodium trimethylsilanolate according to the procedure of Laganis and Ehenard (*Tetrahedron Lett.* 1984, 25, 5831).

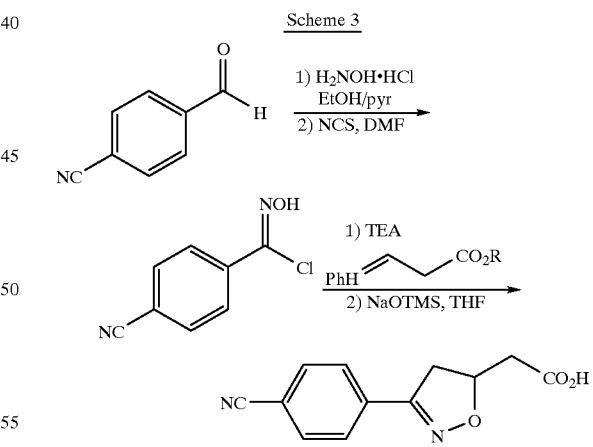

Scheme 3

Alternatively, the dipolar cycloaddition of the hydroximinoyl choride intermediate of Scheme 3 may be reacted with alkyl esters of suitably substituted alkenes, (Scheme 3a ). The oxoesters of 3-butenoic acids may be prepared by initial conversion to the acyl chloride by the method of Marson etal. (*J. Org. Chem.* 1994, 59, 291) followed by condensation with the desired alcohol. This is then submitted to the previously described isoxazoline cyclization conditions to form the ring and is then converted to the thioester by the reaction of the oxoester with (alkylthio)trimethylsilane, prepared by the method of Aizpurua etal. (*Can. J. Chem.* 1984, 62, 336), and aluminum trichloride in tetrahydrofuran by the method of Mukaiyama etal. (*Chem. Lett.* 1974, 187).

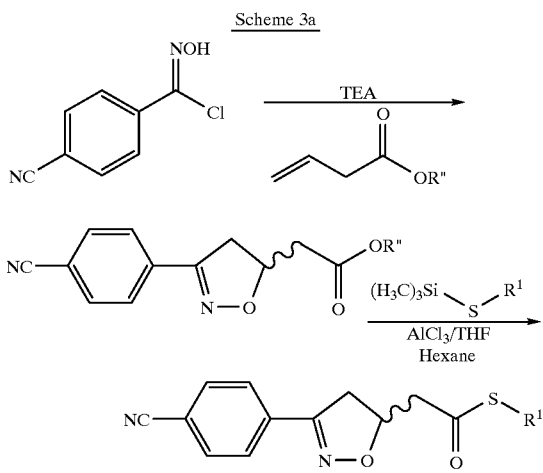

Scheme 3a

Another preparation of the thioesters concerns the condensation of the acyl chloride of the oxazoline substituted carboxylic acid, (prepared as in Scheme 3 or by the cycloaddition of the hydroximinoyl choride intermediate of Scheme 3 with 3-butenoic acid) with either the copper salt of the desired thiol, (salt prepared by the method of Adams etal. (*Org. Syn.* 1962, 42, 22)) by the method of Reissig and Scherer (*Tetrahedron Lett.* 1980, 21, 4259), or condensation with the thiol by cobalt (II) chloride catalysis by the method of Ahmad and Iqbal (*Tetrahedron Lett.* 1986, 27, 3791), (Scheme 3b).

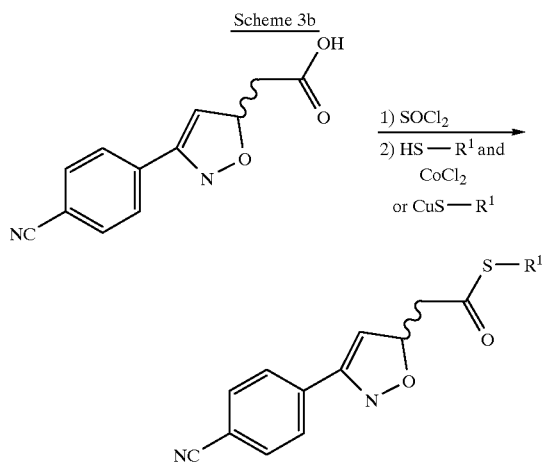

Scheme 3b

The cycloaddition may also be conducted with the thioester of the butenoic acid as in Scheme 3c using similar chemistry to that descibed above.

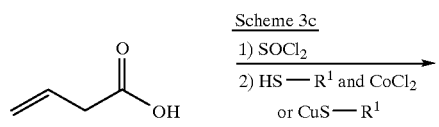

Scheme 3c

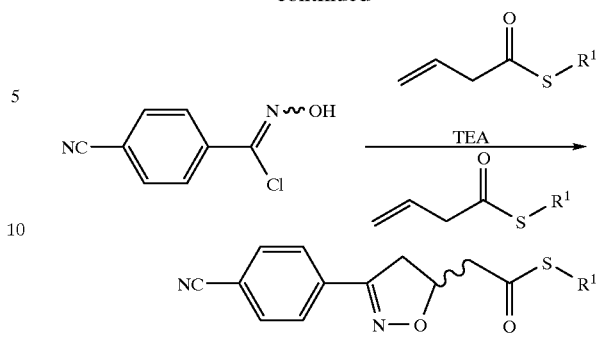

It is recognized that one skilled in the art can prepare substituted isoxazoline compounds of formula (I) from starting materials containing an aldehyde following methods similar to those described in Scheme 3 and exemplified above or by any one of numerous methods published in the literature. Published examples of isoxazoline compounds or processes for making isoxazoline compounds include, but are not limited to, U.S. Pat. No. 4,970,297, U.S. Pat. No. 5,489,562, U.S. Pat. No. 4,256,898, U.S. Pat. No. 4,933,464, U.S. Pat. No. 4,952,700, PCT International Publication WO 95/14681, PCT International Publication WO 95/14680, and PCT International Publication WO 95/24398. Additional published examples of isoxazoline compounds or processes for making isoxazoline compounds can be found in *Comprehensive Organic Synthesis* (Trost ed.) Pergamon Press, New York, 4, 1991, and *The Chemistry of Heterocyclic Compounds: Five and Six-Membered Compounds with Nitrogen and Oxygen* (Wiley ed.) Interscience Publishers, J. Wiley & Sons, New York, 1962.

The following examples are meant to be illustrative of the present invention. These examples are presented to exemplify the invention and are not to be construed as limiting the invention's scope.

HPLC CONDITIONS A 25 cm×4.6 mm Zorbax® RXC8 column, temperature 40° C. (Rockland Technology Inc.); 280 nm; solvent system: A is 0.1% trifluoroacetic acid in water, B is 20% trifluoroacetic acid in acetonitrile, ratio of A/B is 80/20 at T=0 min, 25/75 at T=10 min, 80/20 at T=20 min; 1.00 mL/ min; 2.0 uL injection of ~1 mg/1.0 mL solution.

HPLC CONDITIONS B 25 cm×4.6 mm Bakerbond Chiralcel® OJ 10 um column (Daicel Chemical Industry Limited); temperature 38° C.; 280 nm; solvent system is ethanol/hexane/trifluoroacetic acid (20/85/0.25); 2.0 uL injection of ~1 mg/1.0 mL solution; 0.90 mL/min.

HPLC CONDITIONS C

Same conditions as HPLC CONDITION B except solvent ratio is ethanol/hexane/trifluoroacetic acid 60/40/0.25 and the flow rate is 0.50 mL/min.

HPLC CONDITIONS D

Bakerbond Chiralcel® AS (250×4.6 mm; 10 micron particles), temperature 25° C., 280 nm; solvent system: 85% carbon dioxide, 15% ethanol containing 1% (v/v) trifluoroacetic acid; pressure: 200 atm; flow rate 1.0 mL/min; 5 uL injection of ~1 mg/1 mL solution. Retention times: (R)-(IIa) (11.6 min), (S)-(IIa) (14.0 min), (S)-(IV) (7.4 min), (R)-(IV) (6.7 min).

EXAMPLE 1
Preparation of Compound Ia wherein $R^1$ is n-propyl.

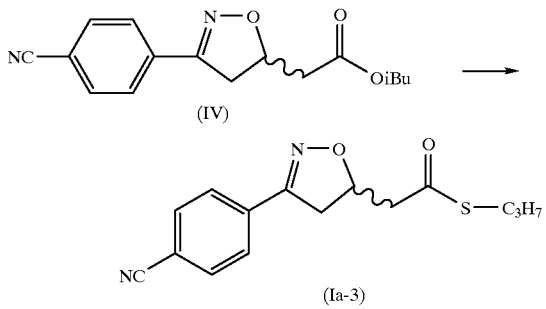

To a solution of 1-propanethiol (98.0 g, 1.29 mol) and THF (850 mL) at 4° C. was added a 2.6 M solution of hexyl lithium in hexanes (500 mL, 1.30 mol) while maintaining the temperature at <15° C. The temperature is lowered to 4° C. and chlorotrimethylsilane (175 mL, 1.38 mol) was added while maintaining the temperature at <15° C. The slurry was warmed to ambient temperature, filtered, and the solids washed with 1:1 THF/hexanes (100 mL). The filtrate was cooled to 10° C. and charged with aluminum chloride (120 g, 0.70 mol) while maintaining the temperature at <21° C. After (IV) (200.0 g, 0.70 mol) was charged, the slurry was heated to reflux over 20 min and maintained at reflux until HPLC (Conditions A) indicated reaction completion after 50 min. The reaction mixture was cooled to 16° C. Water (850 mL) was charged at <30° C. followed by toluene (525 mL). The layers were separated and the aqueous layer further extracted with toluene (100 mL). The combined organic layers were washed with water (3×400 mL), filtered, and heated to 40° C. Heptane (1300 mL) was added at 38–40° C. to crystallize out the thioester. The slurry was cooled to 4° C. over 3 h, filtered, and the solids washed with heptane. The crystals were dried to (Ia-3) (189.5 g, 94%) as a pale yellow granular solid. An analytical sample was prepared by recrystallization from ethyl acetate/heptane. m.p. 67.1–68.2° C.; $^1$H NMR(CDCl$_3$, 300 MHz): 1.00(t, 3H), 1.50–1.70(m, 2H), 2.80–2.95(m, 3H), 3.05–3.10(m, 2H), 3.50–3.60(dd, 1H), 5.05–5.15(m,1H), 7.60–7.80(m, 4H). Anal. Calcd. for $C_{15}H_{16}N_2O_2S$ (288.33): C, 62.48; H, 5.59; N,9.71; S,11.11. Found C,62.38; H, 5.58; N, 9.67; S, 11.03. HRMS (NH$_3$—Cl) m/z 289.101399 (M+H), calc for $C_{15}H_{16}N_2O_2S$ 289.101075.

EXAMPLE 2
Preparation of Compound Ia wherein $R^1$ is n-butyl.

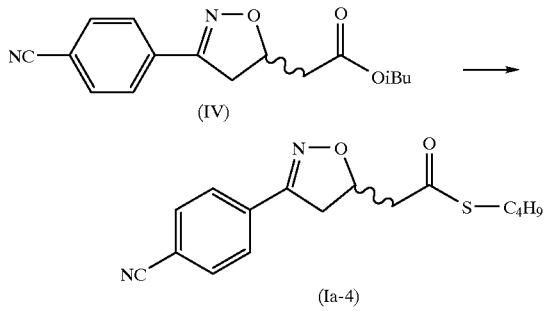

By using the same method as Example 1, (IV) (11.5 g, 40.0 mmol) was treated with AlCl$_3$ (6.8 g, 52 mmol) and n-butylthiotrimethylsilane (prepared in a similar manner to that described in Example 1 from 1-butanethiol) to produce n-butylthioester (Ia-4) (10.6 g, 88%) as white solids. An analytical sample was prepared by recrystallization from ethyl acetate/heptane. m.p. 68.1–69.0° C. $^1$H NMR(CDCl$_3$, 300 MHz): 7.73(q, 4H), 5.3–5.1(m, 1H), 3.52(dd, 1H), 3.3–3.0(m 2H), 3.0–2.8(m, 3H), 1.55(q, 2H), 1.38(h, 2H), 0.92(t, 3H) Anal. calcd. for $C_{16}H_{18}N_2O_2S$ (302.34): C, 63.55; H, 6.00; N, 9.26; S, 10.60. Found: C, 63.62; H, 5.89; N, 9.20; S, 10.63. HRMS (NH$_3$—Cl) m/z 303.116758 (M+H), calc for $C_{16}H_{18}N_2O_2S$ 303.116725.

EXAMPLE 3
Preparation of ±(IIa) from (IV).

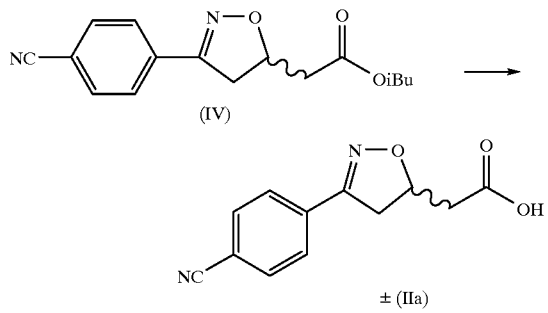

A solution of (IV) (5.64 g, 19.70 mmol), lithium hydroxide monohydrate (0.92 g, 21.93 mmol), methanol (10 mL), THF (30 mL), and water (10 mL) at 0° C. was stirred for 130 min until HPLC (conditions A) indicated the hydrolysis was complete. The mixture was acidifed with 1 N HCl to pH 7. The volatiles were removed under vacuum and the residue further acidified to pH 1 with conc HCl, total volume ~30 mL. The solids were collected by filtration, washed with water, and dried to ±(IIa) (4.42 g, 97%) as a pale yellow powder. The purity and non-chiral spectral properties were the same as that recorded for (R)-(IIa).

EXAMPLE 4
Preparation of methyl ester from ±(IIa).

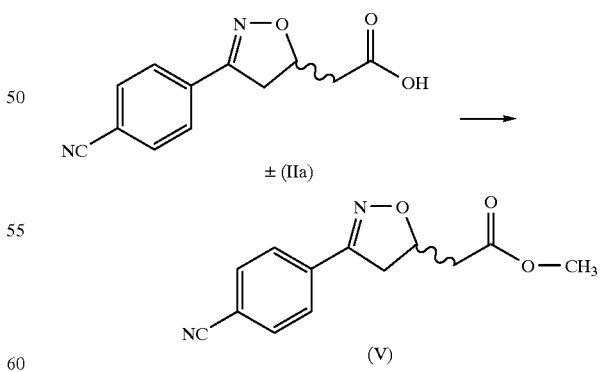

A slurry of ±(IIa) (4.00 g, 17.4 mmol) in methanol (100 mL) at 0° C. was treated with thionyl chloride (2,0 g, 16.8 mmol) and allowed to warm to ambient temperature. After 28 hours, the volatiles were removed under vacuum to leave the methyl ester (V) (4.25 g, 100%) as a yellow powder.

EXAMPLE 5

Preparation of n-propylthioester (Ia-3) from ±(IIa).

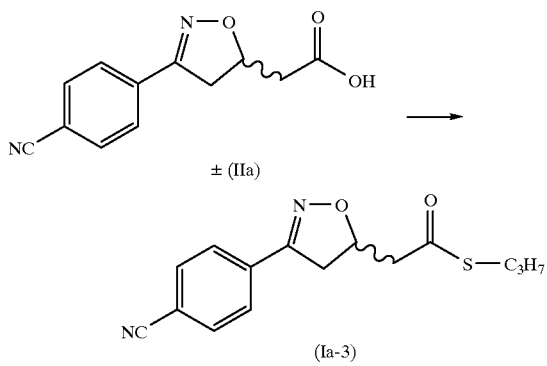

±(IIa)

(Ia-3)

A solution of ±(IIa) (8.0 g, 34.9 mmol), thionyl chloride (9.6 g, 81 mmol), and acetonitrile (100 mL) was stirred at 50° C. for 0.5 h under $N_2$. The solvent and excess thionyl chloride was removed under vacuum and the residue was redissolved into 100 ml of acetonitrile. The solution was treated with $CuSCH_2CH_2CH_3$ (6.2 g, 45.3 mmol), prepared in a similar manner as described previously for the butyl analog (R. Adams etal. Org. Synth. 42, 22), at 50° C. for 2 h under $N_2$. The mixture was evaporated under vacuum to dryness. The solvents were removed under vacuum, the resulting yellow brown solids were mixed with ethyl acetate (100 mL), and the mixture was filtered. The filtrate was washed with 0.1 N HCl (2×100 mL). The organic was dried over $MgSO_4$, filtered, and evaporated to dryness. The resulting solids were dried under vacuum to (Ia-3) (7.2 g, 72%) as yellow solids.

EXAMPLE 6

Preparation of ethylthioester (Ia-2).

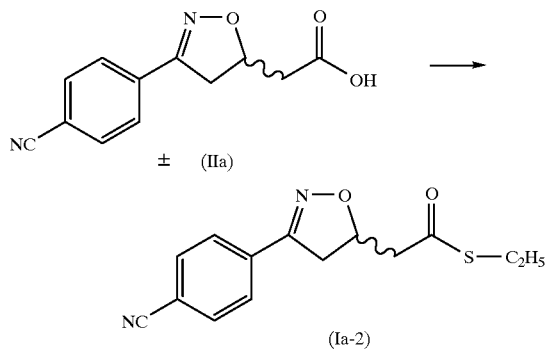

± (IIa)

(Ia-2)

By using a similar method as Example 16, ±(IIa) (4.0 g 17.4 mmol) was reacted with thionyl chloride (5.2 g, 44 mmol) followed by $CuSCH_2CH_3$ (3.2 g, 26 mmol) to produce ethylthioester (Ia-2) (3.1 g, 65%) as yellowish solids. An analytical sample was prepared by recrystallization from ethyl acetate/heptane. m.p. 92.0–93.1° C. $^1H$ NMR($CDCl_3$, 300 MHz) 1.20–1.30(t, 3H), 2.80–3.0(m, 3H), 3.10–3.22(m, 3H), 3.50–3.60(dd, 1H), 5.05–5.15(m, 1H), 7.70–7.80(dd, 4H) Anal. calcd. for $C_{14}H_{14}N_2O_2S$ (274.32): C, 61.29, H, 5.14; N, 10.21; S, 11.68. Found C, 61.45; H, 5.23; N, 10.15, S, 11.96. HRMS ($NH_3$—CI) m/z 275.085274 (M+H), calc for $C_{14}H_{14}N_2O_2S$ 275.085425.

EXAMPLE 7

Preparation of methyl ester (V) from (IV).

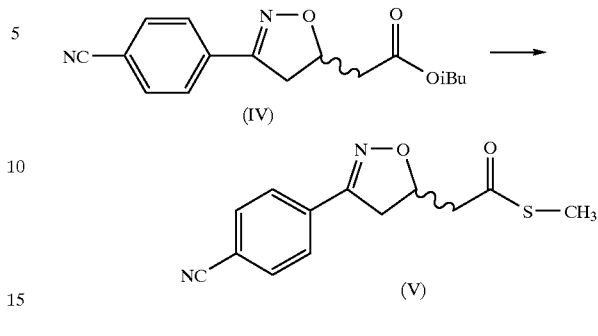

(IV)

(V)

A slurry of (IV) (1.00 g, 3.49 mmol) in methanol (10 mL) at 0° C. was treated with thionyl chloride (0.31 mL, 4.25 mmol) and allowed to warm to ambient temperature. After 3 days, the volatiles were removed under vacuum to the methyl ester (V) (0.88 g, 100%).

EXAMPLE 8

Conversion of methyl ester (V) to ethyl thioester (Ia-2).

This could be done in the same manner as the conversion of (IV) to (Ia-3), in Example 1, in 98% yield. The purity and spectral properties were the same as that of ethyl thioester prepared in Example 6.

EXAMPLE 9

Preparation of n-propylthioester of vinyl acetic acid.

A solution of thionyl chloride (8.4 g, 71 mmol) and vinylacetic acid (5.0 g, 58 mmol) was stirred at room temperature for 10 min and then heated to 50° C. for 4 h. The resulting solution was treated with anhydrous $CoCl_2$ (0.20 g, 1.7 mmol) and 1-propanethiol (4.8 g, 63 mmol). The mixture was stirred at room temperature over night under nitrogen. The mixture was poured into 1:1 water:ethyl acetate (200 mL). The organic layer was separated and the aqueous layer was extracted with 15 mL of ethyl acetate. The combined organic phases were washed with 0.5 M $K_2HPO_4$ solution (3×50 mL) and then 50 mL of water. The solvent was removed under vacuum and the residue was chromatographed on silica gel with hexane to the n-propylthioester of vinyl acetic acid (4.8 g, 57%) as colorless oil. $^1H$ NMR ($CDCl_3$, 300 MHz): 0.9–1.0(t, 3H), 1.5–1.7(m, 2H), 2.8–2.9 (t, 2H), 3.15(d, 2H), 5.08–5.15(m, 2H), 5.8–6.0(m, 1H). Anal. calcd. for $C_7H_{12}OS$ (144.23) C, 58.29; H, 8.38. Found C, 57.93; H, 8.03.

EXAMPLE 10

Cycloaddtion of n-propylthioester of vinyl acetic acid with p-cyanobenzaldehyde to form (Ia-3).

A mixture of the chloro oxime of p-cyanobenzaldehyde (2.10 g, 11.63 inmol), propyl thioester of vinyl acetic acid (2.01 g, 12.00 mmol) and DMF (20 mL) at 0° C. was treated with triethylamine (1.24 g, 12.25 mmol) in 4 mL of DMF over 145 min. The mixture was allowed to warm to ambient temperature and stirred for another 1.5 h. The salts were removed by filtration and washed with 5 mL DMF. The filtrate was added dropwise to 160 mL of dilute HCl to precipitate solids, cooled to 4° C., and collected by filtration. The solids were dried under vacuum to (Ia-3) (1.95 g, 59%) as pale yellow granular solids. The purity is similar and the spectral properties the same as material derived from (IV).

EXAMPLE 11
Preparation of methyl ester (V) via cycloaddition.

The cycloaddition was run in a manner similar to that of Example 10 except in that methyl 3-butenoate (0.93 g, 9.29 mmol) was used as the vinyl acetic acid derivative to produce the methyl ester (V) (1.39 g, 54% yield based on 76% product purity based on HPLC, Conditions A). An analytical sample was prepared by recrystallization from ethyl acetate/heptane. m.p. 121.0–123.3° C.; $^1$H NMR (CDCl$_3$, 300 MHz): 7.65(q, 4H), 5.3–5.1(m, 1H), 3.69(s, 3H), 3.52(dd, 1H), 3.11(dd, 1H), 2.86(dd, 1H), 2.65(dd, 1H). Anal. calcd. for C$_{13}$H$_{12}$N$_2$O$_3$S (244.25): C, 63.93, H, 4.95; N, 11.47; Found C, 63.92; H, 5.04; N, 11.43. HRMS (NH$_3$—CI) m/z 245.092772 (M+H), calc for C$_{13}$H$_{12}$N$_2$O$_3$S 245.092617.

EXAMPLE 12
Lipase screen

Lipases were screened for efficacy for thioester hydrolysis by charging a 2 dram vial with mixtures of the following approximate ratios:

30 mg thioester of compound (IIa)

20 mg lipase 3 mL of pH 8 phosphate buffer 5 uL racemization agent, an organic amine 4 drops Triton® X-100

This mixture was agitated with a small Teflon® coated stir bar in an oil bath at 40–45° C. and monitored by HPLC (conditions A, B, or C).

EXAMPLE 13
Hydrolysis of (Ia-2) to (R)-(IIa) by Amano lipase AK.

The lipase screen technique of Example 12 was used, (the racemization agent was DBU). HPLC (Conditions C) indicated 90–95% of the (R) ester had been hydrolyzed to (R)-(IIa), (remainder of R peak was too small to integrate).

EXAMPLE 14
Hydrolysis of (Ia) wherein Y-R$^1$ is S-isobutyl to (R)-(IIa) by Amano lipase AY30.

The lipase screen technique of Example 12 was used, (the racemization agent was DBU). HPLC (conditions D) ndicated an ee% of 63% for (R)-(IIa).

EXAMPLE 15
Hydrolysis of (Ia) wherein Y-R$^1$ is S-isobutyl to (R)-(IIa) by Amano lipase AK.

The lipase screen technique of Example 12 was used, (the racemization agent was DBU). HPLC (conditions D) indicated an ee% of 85% for (R)-(IIa).

EXAMPLE 16
Hydrolysis of (Ia-4) to (R)-(IIa) by Amano lipase AK.

The lipase screen technique of Example 12 was used, (the racemization agent was DBU). HPLC (conditions D) indicated an ee% of 95% for (R)-(IIa).

EXAMPLE 17
Hydrolysis of (Ia-4) to (R)-(IIa) by Amano lipase PS30.

The lipase screen technique of Example 12 was used, (the racemization agent was DBU). HPLC (conditions D) indicated an ee% of 87% for (R)-(IIa).

EXAMPLE 18
Dynamic Resolution of (Ia-3) to (R)-(IIa).

A solution of water (2.7 L), NaH$_2$PO$_4$ (275 g, 2.29 mol), and 25% aqueous trimethylamine (330 mL, 1.27 mol) was adjusted to pH 8.35 with 6N NaOH (80 mL). To the resulting solution was charged (Ia-3) (183.0 g, 0.635 mol), Triton® X100 (15 g), and lipase PS30 (18.3 g). This suspension was stirred at 40–42° C. and the pH was maintained between 9.0 to 9.5 by adding 6 N NaOH solution occasionally. The reaction was monitored by HPLC (condition C) for 2 days until complete conversion (>99.5% by area) of (Ia-3) to (R)-(IIa) had occurred. The mixture was cooled to ambient temperature and the solids (lipase) were removed by filtration. (R)-(IIa) was precipitated by the addition of 50% H$_3$PO$_4$ (450 mL) until the pH reached 3. The solids were collected by filtration and washed two times with 200 mL water. The solids were dried under vacuum to produce 143.0 g (98.3%ee, HPLC condition B) of yellowish solids. This was dissolved into 2 L of ethanol and recrystallized by cooling to 3° C. The crystals were collected by filtration, washed with ethanol (200 mL), and dried under vacuum to (R)-(IIa) (129.4 g, 89%), as a shiny powder. m.p 198–200° C.; 99.7% ee (HPLC conditions D) . $^1$H NMR (DMSO-d$_6$, 300 MHz) 12.46(s, 1H), 7.89(q, 4H), 5.15–4.95(m, 1H), 3.63(dd, 1H) , 3.20(dd, 1H) , 2.70(m, 2H) . Anal. Calcd for C$_{12}$H$_{10}$N$_2$O$_4$ (230.22) C, 62.61; H, 4.38; N, 12.17. Found: C, 62.39; H,4.49; N, 11.98.

EXAMPLE 19
Dynamic Resolution of (Ia-2) to (R)-(IIa).

By using the same conditions as described in Example 18, 1.0 g (3.48 mmol) of ethylthioester (Ia-2) was hydrolysed to (R)-(IIa) (0.63 g, 75%) as off-white crystals, (97.3% ee, HPLC conditions D).

EXAMPLE 20
Dynamic Resolution of (Ia-4) to (R)-(IIa).

By using the same conditions as described in Example 18, 5.0 g (15.8 mmol) of n-butylthioester (Ia-4) was hydrolyzed to (R)-(IIa) (3.38 g, 91.4%) as colorless needles, (99.4% ee, HPLC conditions D).

EXAMPLE 21
Dynamic Resolution of (Ia-2) using ethylamine instead of trimethylamine as racemization agent.

By using the similar conditions to those described in Example 18, 2.0 g (7.3 mmol) of ethylthioester (Ia-2) was hydrolyzed in the presence of 70% aqueous ethylamine (0.33 g, 5.12 mmol) to (R)-(IIa) (0.78 g, 45%) as white crystals, (92.4% ee, HPLC conditions D).

EXAMPLE 22
Dynamic Resolution of (Ia-3) in the absence of buffer.

(Ia-3) (0.90 g, 3.12 mmol) was hydrolyzed in a manner similar to that of Example 18 except no buffer was charged and 1 N HCl was added after the trimethylamine addition in order to lower the pH to 9.5. Following a typical workup, (R)-(IIa) (0.42 g, 58%) was recovered as a white solid, (98.8% ee, HPLC conditions B).

EXAMPLE 23
Dynamic Resolution of (Ia-3) to (R)-(IIa) in the absence of surfactant.

(Ia-3) (10.0 g, 34.9 mmol) was hydrolyzed in a manner similar to that of Example 18 except no surfactant was charged. Following a typical workup, (R)-(IIa) (7.4 g, 92%) was recovered as a white solid, (98.2% ee, HPLC conditions B).

What is claimed is:

1. A process for preparation of an optically active compound of Formula (R)-(II) or Formula (S)-(II):

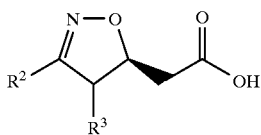

(R)-(II)

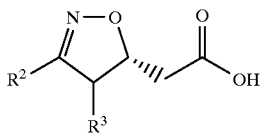

(S)-(II)

or a salt form thereof, wherein:

$R^2$ is —H, halo, —$CF_3$, —CN, —$NO_2$, —OH, $C_1$-$C_8$ alkoxy, $C_1$-$C_{10}$ alkylcarbonyl, —N($R^{12}$)$R^{13}$, —CHO, —$CO_2$H, —C(=O)$R^{5a}$, —CONR$^5$R$^{5a}$, —C(=NH)NR$^5$R$^{5a}$, —SR$^{5a}$, —$SO_2$R$^{5a}$, —$SO_2$NR$^5$R$^{5a}$, $C_1$-$C_8$ alkyl substituted with 0-3 $R^4$, $C_2$-$C_8$ alkenyl substituted with 0-3 $R^4$, $C_2$-$C_8$ alkynyl substituted with 0-2 $R^4$, $C_3$-$C_{10}$ cycloalkyl substituted with 0-3 $R^4$, $C_6$-$C_{10}$ aryl substituted with 0-3 $R^4$, a 5–10 membered heterocyclic ring consisting of 1–4 N, O, or S heteroatoms, wherein said heterocyclic ring may be saturated, partially saturated, or fully unsaturated, said heterocyclic ring being substituted with 0-2 $R^4$, an amino acid, or a peptide;

$R^3$ is hydrogen, $C_1$-$C_4$ alkyl substituted with 0-3 $R^4$, or phenyl substituted with 0-3 $R^4$;

$R^4$ is selected from H, $C_1$-$C_{10}$ alkyl, —OH, $C_1$-$C_{10}$ alkoxy, —$NO_2$, $C_1$-$C_{10}$ alkylcarbonyl, —N($R^{12}$)$R^{13}$, —CN, halo, —$CF_3$, —CHO, —$CO_2$H, —C(=O)$R^{5a}$, —CONR$^5$R$^{5a}$, —C(=NH)NR$^5$R$^{5a}$, —OC(=O)$R^{5a}$, —OR$^{5a}$, —OC(=O)NR$^5$R$^{5a}$, —OCH$_2$CO$_2$H, —CO$_2$CH$_2$CO$_2$H, —NR$^{5a}$C(=O)R$^{5a}$, —NR$^{5a}$C(=O)OH, —NR$^{5a}$C(=O)NR$^5$R$^{5a}$, —NR$^{5a}$SO$_2$NR$^5$R$^{5a}$, —NR$^{5a}$SO$_2$R$^5$, —SR$^{5a}$, —SO$_2$R$^{5a}$, —SO$_2$NR$^5$R$^{5a}$, $C_2$-$C_6$ alkenyl, $C_3$-$C_{11}$ cycloalkyl, $C_4$-$C_{11}$ cycloalkylmethyl or $C_6$-$C_{10}$ aryl optionally substituted with 1–3 groups selected from halogen, $C_1$-$C_4$ alkoxy, $C_1$-$C_4$ alkyl, —$CF_3$, —S(O)$_2$Me, or —NMe$_2$;

$R^5$ is selected from H, $C_1$-$C_8$ alkyl, $C_2$-$C_6$ alkenyl, $C_3$-$C_{11}$ cycloalkyl, $C_4$-$C_{11}$ cycloalkylmethyl, $C_6$-$C_{10}$ aryl, $C_7$-$C_{11}$ arylalkyl, or $C_1$-$C_{10}$ alkyl substituted with 0-2 $R^6$;

$R^{5a}$ is selected from H, $C_1$-$C_8$ alkyl, $C_2$-$C_6$ alkenyl, $C_3$-$C_{11}$ cycloalkyl, $C_4$-$C_{11}$ cycloalkylmethyl, $C_6$-$C_{10}$ aryl, $C_7$-$C_{11}$ arylalkyl, or $C_1$-$C_{10}$ alkyl substituted with 0-2 $R^6$;

alternately, $R^5$ and $R^{5a}$ can be taken together to be 3-azabicyclononyl, 1-piperidinyl, 1-morpholinyl or 1-piperazinyl, each being optionally substituted with $C_1$-$C_6$ alkyl, $C_6$-$C_{10}$ aryl, $C_7$-$C_{11}$ arylalkyl, $C_1$-$C_6$ alkylcarbonyl, $C_3$-$C_7$ cycloalkylcarbonyl, $C_1$-$C_6$ alkylsulfonyl or $C_6$-$C_{10}$ arylsulfonyl;

$R^6$ is selected from H, $C_1$-$C_{10}$ alkyl, hydroxy, $C_1$-$C_{10}$ alkoxy, nitro, $C_1$-$C_{10}$ alkylcarbonyl, or —N($R^{12}$)$R^{13}$;

$R^{12}$ and $R^{13}$ are independently selected from H, methyl, or ethyl;

said process comprising:

contacting, in a suitable solvent, a stereoisomeric mixture of a compound of Formula (I)

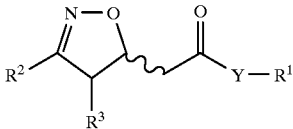

(I)

wherein:

Y is S;

$R^1$ is —C($R^{10}$)$_2$($R^{10a}$),

—C($R^{10}$)$_2$—C($R^{10b}$)$_2$($R^{10c}$),

—C($R^{10}$)$_2$—C($R^{10b}$)$_2$—C($R^{10c}$)$_3$,

—C($R^{10}$)$_2$—C($R^{10b}$)=C($R^{10c}$)$_2$,

—C($R^{10}$)$_2$—C≡C($R^{10c}$),

—C($R^{10}$)=C($R^{10b}$) ($R^{10c}$),

—C($R^{10}$)=C($R^{10b}$)—C($R^{10c}$)$_3$,

—C≡C($R^{10c}$),

—C≡C—C($R^{10c}$)$_3$, $R^{10}$ is H or F;

$R^{10a}$ is selected from H, F, Cl, Br, —CH$_3$, —CH$_2$CH$_3$, —CH$_2$CH$_2$CH$_3$, —CF$_3$, —CF$_2$CF$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, and cyclopropyl;

$R^{10b}$ is H, F, Cl, or Br;

$R^{10c}$ at each occurrence is, independently, selected from H, halo, $C_1$-$C_3$ haloalkyl, —OH, $C_1$-$C_4$ alkoxy, —CF$_3$, —SCH$_3$, —SCH$_2$CH$_3$, —SCH$_2$CH$_2$CH$_3$, —CN, —NO$_2$, —S(O)$_2$Me, —NMe$_2$, $C_1$-$C_6$ alkyl substituted with 0-3 $R^{11}$, $C_2$-$C_6$ alkenyl substituted with 0-3 $R^{11}$, $C_2$-$C_6$ alkynyl substituted with 0-2 $R^{11}$, $C_3$-$C_6$ cycloalkyl substituted with 0-3 $R^{11}$, $C_6$-$C_{10}$ aryl substituted with 0-3 $R^{11}$, or $C_4$-$C_{10}$ heterocycle substituted with 0-3 $R^{11}$; and $R^{11}$ is selected from the group H, halo, $C_1$-$C_4$ alkyl, $C_1$-$C_3$ haloalkyl, $C_1$-$C_4$ alkoxy, phenyl, —OH, —NO$_2$, —CN, —CF$_3$, —S(O)$_2$Me, and —NMe$_2$;

with a suitable lipase in the presence of a racemization agent, while maintaining a suitable basic pH by addition of a base or an acid, to form a compound of formula (R)-(II) or formula (S)-(II) in greater than 51% yield and greater than 80% optical purity.

2. A process of claim 1 for preparation of an optically active compound of Formula (R)-(II):

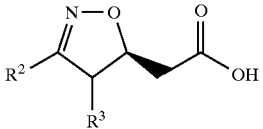

(R)-(II)

or a salt form thereof, wherein:

$R^2$ is phenyl substituted with 0-3 $R^4$, $R^3$ is hydrogen;

$R^4$ is selected from H, $C_1$-$C_{10}$ alkyl, —OH, $C_1$-$C_{10}$ alkoxy, —NO$_2$, $C_1$-$C_{10}$ alkylcarbonyl, —N($R^{12}$)$R^{13}$, —CN, halo, —CF$_3$, —CHO, —CO$_2$H, —C(=O)R$^{5a}$, —CONR$^5$R$^{5a}$, —C(=NH)NR$^5$R$^{5a}$, —OC(=O)R$^{5a}$, —OR$^{5a}$, —OC(=O)NR$^5$R$^{5a}$, —OCH$_2$CO$_2$H, —CO$_2$CH$_2$CO$_2$H, —NR$^{5a}$C(=O)R$^{5a}$, —NR$^{5a}$C(=O)OH, —NR$^{5a}$C(=O)NR$^5$R$^{5a}$, —NR$^{5a}$SO$_2$NR$^5$R$^{5a}$, —NR$^{5a}$SO$_2$R$^5$, —SO$_2$R$^{5a}$, —SO$_2$NR$^5$R$^{5a}$, C$_2$–C$_6$ alkenyl, C$_3$–C$_{11}$ cycloalkyl, C$_4$–C$_{11}$ cycloalkylmethyl or
C$_6$–C$_{10}$ aryl optionally substituted with 1–3 groups selected from halogen, C$_1$–C$_4$ alkoxy, C$_1$–C$_4$ alkyl, —CF$_3$, —S(O)$_2$Me, or —NMe$_2$;
R$^5$ is selected from H, C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0-2 R$^6$;
R$^{5a}$ is selected from H, C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0-2 R$^6$;
alternately, R$^5$ and R$^{5a}$ can be taken together to be 3-azabicyclononyl, 1-piperidinyl, 1-morpholinyl or 1-piperazinyl, each being optionally substituted with C$_1$–C$_6$ alkyl, C$_6$–C$_{10}$ aryl, C$_7$–C$_{11}$ arylalkyl, C$_1$–C$_6$ alkylcarbonyl, C$_3$–C$_7$ cycloalkylcarbonyl, C$_1$–C$_6$ alkylsulfonyl or C$_6$–C$_{10}$ arylsulfonyl;
R$^6$ is selected from H, C$_1$–C$_{10}$ alkyl, hydroxy, C$_1$–C$_{10}$ alkoxy, nitro, C$_1$–C$_{10}$ alkylcarbonyl, or —N(R$^{12}$)R$^3$;
R$^{12}$ and R$^{13}$ are independently selected from H, methyl, or ethyl;
said process comprising:
contacting, in a suitable solvent, a stereoisomeric mixture of a compound of Formula (I):

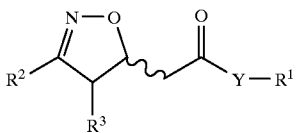

(I)

wherein:
Y is S;
R$^1$ is —C(R$^{10}$)$_2$(R$^{10a}$),
—C(R$^{10}$)$_2$—C(R$^{10b}$)$_2$(R$^{10c}$),
—C(R$^{10}$)$_2$—C(R$^{10b}$)$_2$—C(R$^{10c}$)$_3$,
—C(R$^{10}$)$_2$—C(R$^{10b}$)=C(R$^{10c}$)$_2$,
—C(R$^{10}$)$_2$—C≡C(R$^{10c}$),
—C(R$^{10}$)=C(R$^{10b}$)(R$^{10c}$),
—C(R$^{10}$)=C(R$^{10b}$)—C(R$^{10c}$)$_3$,
—C≡C(R$^{10c}$),
—C≡C—C(R$^{10c}$)$_3$,
R$^{10}$ is H or F;
R$^{10a}$ is selected from H, F, Cl, Br, —CH$_3$, —CH$_2$CH$_3$, —CH$_2$CH$_2$CH$_3$, —CF$_3$, —CF$_2$CF$_3$, —OCH$_3$, —OCH$_2$CH$_3$, —OCH$_2$CH$_2$CH$_3$, —SCH$_3$, —SCH$_2$CH$_3$, —SCH$_2$CH$_2$CH$_3$, and cyclopropyl;
R$^{10b}$ is H, F, Cl, or Br;
R$^{10c}$ at each occurrence is, independently, selected from H, halo, C$_1$–C$_3$ haloalkyl, —OH, C$_1$–C$_4$ alkoxy, —CF$_3$, —SCH$_3$, —SCH$_2$CH$_3$, —SCH$_2$CH$_2$CH$_3$, —NMe$_2$,
C$_1$–C$_6$ alkyl substituted with 0-3 R$^{11}$,
C$_2$–C$_6$ alkenyl substituted with 0-3 R$^{11}$,
C$_2$–C$_6$ alkynyl substituted with 0-2 R$^{11}$,
C$_3$–C$_6$ cycloalkyl substituted with 0-3 R$^{11}$,
C$_6$–C$_{10}$ aryl substituted with 0-3 R$^{11}$, or
C$_4$–C$_{10}$ heterocycle substituted with 0-3 R$^{11}$; and
R$^{11}$ is selected from the group H, halo, C$_1$–C$_4$ alkyl, C$_1$–C$_3$ haloalkyl, C$_1$–C$_4$ alkoxy, phenyl, —OH, —NO$_2$, —CN, —CF$_3$, —S(O)$_2$Me, and —NMe$_2$;
with a suitable lipase in the presence of a racemization agent, while maintaining a suitable basic pH by addition of a base or an acid, to form a compound of formula (R)-(II) in greater than 51% yield and greater than 80% optical purity.

3. A process of claim 2 for preparation of an optically active compound of Formula (R)-(IIa):

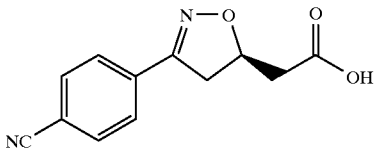

(R)-(IIa)

or a salt form thereof, said process comprising:
contacting, in a suitable solvent, a stereoisomeric mixture of a compound of Formula (Ia):

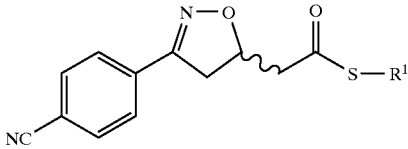

(Ia)

wherein:
R$^1$ is —CH$_2$(R$^{10a}$),
—CH$_2$—CH$_2$(R$^{10c}$),
—CH$_2$—CH$_2$—C(R$^{10c}$)$_3$,
—CH$_2$—CH=C(R$^{10c}$)$_2$,
—CH$_2$—CH≡C(R$^{10c}$)$_2$,
R$^{10a}$ is selected from H, —CH$_3$, —CH$_2$CH$_3$, and —CH$_2$CH$_2$CH$_3$;
R$^{10c}$ at each occurrence is, independently, selected from H, —OH, C$_1$–C$_4$ alkoxy, —NMe$_2$,
C$_1$–C$_6$ alkyl substituted with 0-3 R$^{11}$,
C$_2$–C$_6$ alkenyl substituted with 0-3 R$^{11}$,
C$_2$–C$_6$ alkynyl substituted with 0-2 R$^{11}$, or
C$_3$–C$_6$ cycloalkyl substituted with 0-3 R$^{11}$; and
R$^{11}$ is selected from the group H, halo, C$_1$–C$_4$ alkyl, C$_1$–C$_3$ haloalkyl, C$_1$–C$_4$ alkoxy, —OH, —NO$_2$, —CN, —CF$_3$, —S(O)$_2$Me, and —NMe$_2$;
with a suitable lipase in the presence of a racemization agent, while maintaining a suitable basic pH by addition of a base or an acid, to form a compound of formula (R)-(IIa) in greater than 51% yield and greater than 80% optical purity.

4. A process of claim 3 wherein the suitable lipase is Amano PS30 or Amano AK.

5. A process of claim 3 wherein the racemization agent is selected from the group trimethylamine, triethylamine, tripropylamine and tributylamine.

6. A process of claim 3 wherein the suitable solvent is either water or a mixture of water and organic solvent wherein the organic solvent is selected from the group methanol, ethanol, propanol, isopropanol acetonitrile, toluene, xylene and ether.

7. A process of claim 3 wherein the suitable pH is in the range of about 8.0 to about 11.0.

8. A process of claim 3 further comprising a suitable buffer added to the suitable solvent to assist in maintaining the suitable pH by addition of a base.

9. A process of claim 8 wherein the suitable lipase is Amano PS30 or Amano AK.

10. A process of claim 8 wherein the racemization agent is selected from the group trimethylamine, triethylamine, tripropylamine and tributylamine.

11. A process of claim 8 wherein the suitable solvent is either water or a mixture of water and organic solvent wherein the organic solvent is selected from the group methanol, ethanol, propanol, isopropanol acetonitrile, toluene, xylene and ether.

12. A process of claim 8 wherein the suitable pH is in the range of about 8.0 to about 11.0.

13. A process of claim 8 for the preparation of an optically active compound of Formula (R)-(IIa):

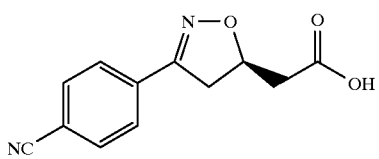
(R)-(IIa)

or a salt form thereof, said process comprising:
contacting, in water, in which is dissolved a suitable buffer, a stereoisomeric mixture of a compound of Formula (Ia):

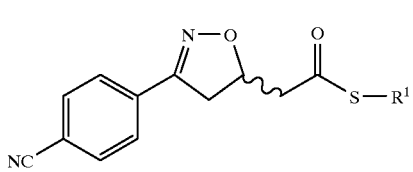
(Ia)

wherein $R^1$ is n-propyl;
with the lipase Amano PS30 in the presence of racemization agent trimethylamine, while maintaining a suitable pH in the range of about 8.0 to about 10.0 by addition of a base or an acid, to form a compound of formula (R)-(IIa) in greater than 51% yield and greater than 80% optical purity.

14. A process of claim 3 further comprising a suitable nonionic, cationic or anionic surfactant added to the suitable solvent.

15. A process of claim 13 wherein the suitable lipase is Amano PS30 or Amano AK.

16. A process of claim 13 wherein the racemization agent is selected from the group trimethylamine, triethylamine, tripropylamine, and tributylamine.

17. A process of claim 13 wherein the suitable solvent is either water or a mixture of water and organic solvent wherein the organic solvent is selected from the group methanol, ethanol, propanol, isopropanol acetonitrile, toluene, xylene, and ether.

18. A process of claim 13 wherein the suitable pH is in the range of about 8.0 to about 11.0.

19. A process of claim 13 wherein the suitable nonionic, cationic or anionic surfactant is PEG(9–10)p-t-octylphenol.

20. A process of claim 13 for the preparation of an optically active compound of Formula (R)-(IIa):

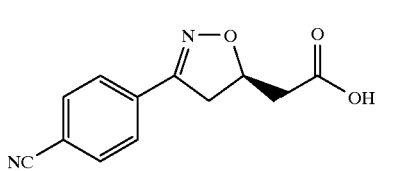
(R)-(IIa)

or a salt form thereof, said process comprising:
contacting, in water, in which is dissolved a suitable nonionic, cationic or anionic surfactant, a stereoisomeric mixture of a compound of Formula (Ia):

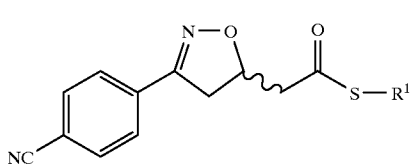
(Ia)

wherein $R^1$ is n-propyl,
with the lipase Amano PS30 in the presence of racemization agent trimethylamine, while maintaining a suitable pH in the range of about 8.0 to about 10.0 by addition of a base or an acid, to form a compound of formula (R)-(IIa) in greater than 51% yield and greater than 80% optical purity.

21. A process of claim 3 wherein:

R is —CH$_2$(R$^{10a}$),

—CH$_2$—CH$_2$(R$^{10c}$),

—CH$_2$—CH$_2$—C(R$^{10c}$)$_3$, $R^{10a}$ is selected from H, —CH$_3$, —CH$_2$CH$_3$, and —CH$_2$CH$_2$CH$_3$;
$R^{10c}$ at each occurrence is, independently, selected from H, —OH, C$_1$–C$_4$ alkoxy, —NMe$_2$,
C$_1$–C$_6$ alkyl substituted with 0-3 $R^{11}$, or
C$_3$–C$_6$ cycloalkyl substituted with 0-3 $R^{11}$; and
$R^{11}$ is selected from the group H, halo, C$_1$–C$_4$ alkyl, C$_1$–C$_3$ haloalkyl, C$_1$–C$_4$ alkoxy, —OH, —NO$_2$, —CN, —CF$_3$, —S(O)$_2$Me, and —NMe$_2$.

22. A process of claim 3 wherein:
$R^1$ is —CH$_2$(R$^{10a}$) or —CH$_2$—CH$_2$(R$^{10c}$),
$R^{10a}$ is selected from H, —CH$_3$, —CH$_2$CH$_3$, and —CH$_2$CH$_2$CH$_3$;
$R^{10c}$ is selected from H, —OH, C$_1$–C$_4$ alkoxy, —NMe$_2$, cyclopropyl, and C$_1$–C$_3$ alkyl substituted with 0-2 $R^{11}$;
$R^{11}$ is selected from the group H, C$_1$–C$_4$ alkyl, C$_1$–C$_4$ alkoxy, —OH, —NO$_2$, —CN, —CF$_3$, —S(O)$_2$Me, and —NMe$_2$;

the suitable lipase is Amano PS30 or Amano AK;
the racemization agent is selected from the group trimethylamine, triethylamine, tripropylamine and tributylamine;
the suitable solvent is either water or a mixture of water and organic solvent wherein the organic solvent is selected from the group methanol, ethanol, propanol, isopropanol acetonitrile, toluene, xylene and ether; and
the suitable pH is in the range of about 8.0 to about 11.0.

23. A process of claim 3 for the preparation of an optically active compound of Formula (R)-(IIa):

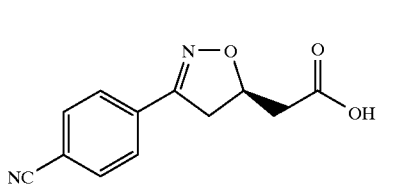
(R)-(IIa)

or a salt form thereof, said process comprising:
contacting, in water, a stereoisomeric mixture of a compound of Formula (Ia):

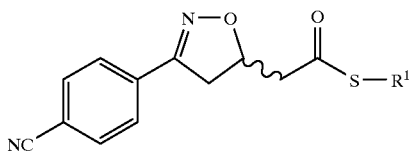

wherein R¹ is ethyl, n-propyl or n-butyl,
with the lipase Amano PS30 in the presence of racemization agent trimethylamine, while maintaining a suitable pH in the range of about 8.0 to about 10.0 by addition of a base or an acid, to form a compound of formula (R)-(IIa) in greater than 51% yield and greater than 80% optical purity.

24. A process of claim 8 further comprising a suitable nonionic, cationic or anionic surfactant added to the suitable solvent.

25. A process of claim 24 for the preparation of an optically active compound of Formula (R)-(IIa):

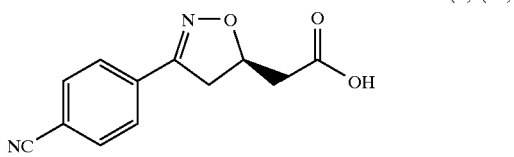

or a salt form thereof, said process comprising:

contacting, in water, in which is dissolved a suitable buffer and a suitable nonionic, cationic or anionic surfactant, a stereoisomeric mixture of a compound of Formula (Ia):

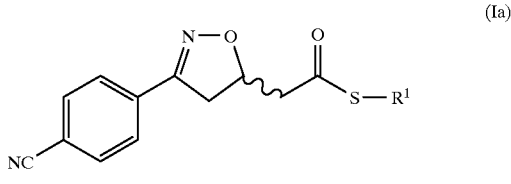

wherein R¹ is n-propyl, with the lipase Amano PS30 in the presence of racemization agent trimethylamine, while maintaining a suitable pH in the range of about 8.0 to about 10.0 by addition of a base, to form a compound of formula (R)-(IIa) in greater than 51% yield and greater than 80% optical purity.

* * * * *

UNITED STATES PATENT AND TRADEMARK OFFICE
CERTIFICATE OF CORRECTION

PATENT NO.    : 6,022,977
DATED         : February 8, 2000
INVENTOR(S)   : Lin-Hua Zhang, Luigi Anzalone, Jaan Pesti, Jianguo Yin It is certified that error appears in the above-identified patent and that said Letters Patent is hereby corrected as shown below:

Column 4,
Line 67, please delete "of" and insert --or--.

Column 20,
Line 63, please delete "etal." and insert --et al.--.

Column 21,
Line 1, please delete "etal." and insert --et al.--.

Column 24,
Line 37, please delete "conc" and insert --conc.--.

Column 28,
Line 28, please delete "hydrolysed" and insert --hydrolyzed--.

Column 31,
Line 19, please delete "-N($R^{12}$)$R^3$;" and insert -- -N($R^{12}$)$R^{13}$--.

UNITED STATES PATENT AND TRADEMARK OFFICE
CERTIFICATE OF CORRECTION

PATENT NO. : 6,022,977
DATED : February 8, 2000
INVENTOR(S) : Lin-Hua Zhang, Luigi Anzalone, Jaan Pesti, Jianguo Yin It is certified that error appears in the above-identified patent and that said Letters Patent is hereby corrected as shown below:

Column 32,
Line 30, please delete "-$CH_2$-CH≡C($R^{10c}$)2," and insert ---$CH_2$-C≡C($R^{10C}$),--.

Column 34,
Line 19, please delete "R is -($CH_2$($R^{10a}$))," and insert -- $R^1$ is -$CH_2$($R^{10a}$),--.

Signed and Sealed this

Third Day of July, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,022,977
DATED : February 8, 2000
INVENTOR(S) : Lin-Hua Zhang, Luigi Anzalone, Jaan Pesti, Jianguo Yin It is certified that error appears in the above-identified patent and that said Letters Patent is hereby corrected as shown below:

Column 13,
Line 46, please delete "Amano AX" and insert -- Amano AK --.

Signed and Sealed this

Eleventh Day of December, 2001

Attest:

NICHOLAS P. GODICI
Attesting Officer  Acting Director of the United States Patent and Trademark Office